US011918659B2

(12) United States Patent
Daunert et al.

(10) Patent No.: US 11,918,659 B2
(45) Date of Patent: Mar. 5, 2024

(54) MATERIALS AND METHODS FOR INDUCING THERAPEUTIC HYPOTHERMIA IN A MAMMALIAN SUBJECT

(71) Applicant: UNIVERSITY OF MIAMI, Miami, FL (US)

(72) Inventors: Sylvia Daunert, Miami, FL (US); Suzana Hamdan, Miami, FL (US); Dalton Dietrich, Miami, FL (US); Sapna Deo, Miami, FL (US); Helen Bramlett, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 301 days.

(21) Appl. No.: 17/277,775

(22) PCT Filed: Sep. 19, 2019

(86) PCT No.: PCT/US2019/051938
§ 371 (c)(1),
(2) Date: Mar. 19, 2021

(87) PCT Pub. No.: WO2020/061315
PCT Pub. Date: Mar. 26, 2020

(65) Prior Publication Data
US 2021/0346515 A1 Nov. 11, 2021

Related U.S. Application Data

(60) Provisional application No. 62/734,121, filed on Sep. 20, 2018.

(51) Int. Cl.
*A61K 47/69* (2017.01)
*A61K 9/00* (2006.01)
*A61K 9/51* (2006.01)

(52) U.S. Cl.
CPC ........ *A61K 47/6929* (2017.08); *A61K 9/0043* (2013.01); *A61K 9/513* (2013.01)

(58) Field of Classification Search
CPC .................... A61K 9/145; A61K 47/6929
See application file for complete search history.

(56) References Cited

U.S. PATENT DOCUMENTS

2009/0197966 A1* 8/2009 Weber .................. A61P 9/12
514/625
2013/0102680 A1 4/2013 Chuang
2017/0216309 A1 8/2017 Blanco et al.

FOREIGN PATENT DOCUMENTS

TW 201302712 A 1/2013

OTHER PUBLICATIONS

Salatin et al., Hydrogel nanoparticles and nanocomposites for nasal drug/vaccine delivery, Arch. Pharm. Res., 39:1181-1192 (2016).
Sanna et al., Targeted therapy using nanotechnology: focus on cancer, Int. J. of Nanomedicine, 9:467-483 (2014).
Shen et al., Interfacial Cohesion and Assembly of Bioadhesive Molecules for Design of Long-Term Stable Hydrophobic Nanodrugs toward Effective Anticancer Therapy, ACS Nano., 10(6):5720-5729 (2016).
Stovner et al., Neurological disorders in the Global Burden of Disease 2010 study, Acta. Neur. Scandinavica., 129:1-6 (2014).
Szolcsanyi, Effect of Capsaicin on Thermoregulation: an Update with New Aspects, Temp. (Austin), 2(2):277-296 (2015).
Talegaonkar et al., Intranasal delivery: An approach to bypass the blood brain barrier, Indian J. of Pharm., 36(3):140-147 (2004).
Thoman et al., The Versatility of Polysorbate 80 (Tween 80) as an Ionophore, Journal of Pharmaceutical Sciences, 88(2): 259 (1998).
Toth et al., Vanilloid Receptor-1 (TRPV1) Expression and Function in the Vasculature of the Rat, J. Histochem. Cytochem., 62(2):129-144 (2014).
Trevisani et al., Targeting TRPVI: Challenges and Issues in Pain Management, The Open Drug Discovery Journal, 2(3):37-49 (2010).
Truettner et al., Posttraumatic therapeutic hypothermia alters microglial and macrophage polarization toward a beneficial phenotype, J. Cerebral Blood Flow & Metabolism, 37(8):2952-2962 (2016).
Vercelli et al., Transient Receptor Potential Vanilloid 1 in animal tissues: An overview to highlight similarities and differences with human species, Recep. & Clini. Inv., 2:1-9 (2015).
Vyklicky et al., Calcium-dependent desensitization of vanilloid receptor TRPV1: a mechanism possibly involved in analgesia induced by topical application of capsaicin, Physiol. Res., 57(Suppl 3):S59-68 (2008).
Wang et al., Capsaicin-loaded nanolipoidal carriers for topical application: design, characterization, and in vitro/in vivo evaluation, International Journal of Nanomedicine, 12:3883-3889 (2017).
Wang et al., Spaced cognitive training promotes training transfer, Front. Hum. Neuroscience, 8:217 (2014).
Wang et al., Therapeutic Hypothermia in Spinal Cord Injury: The Status of Its Use and Open Questions, International Journal of Molecular Sciences, 16(8):16848-16879 (2015).
Wei, Calixarene-encapsulated nanoparticles: self-assembly into functional nanomaterials, Chem. Commun. (Camb)., (15):1581-1591 (2006).
Wu et al., Physical and chemical stability of drug nanoparticles, Adv. Drug Deliv. Rev., 63(6):456-469 (2011).
Yokobori et al., Targeted temperature management in traumatic brain injury, J. of Int. Care, 4:28 (2016).
You et al., Nanocrystals of a new camptothecin derivative WCN-21 enhance its solubility and efficacy, Oncotarget., 8(18):29808-29822 (2017).
Yousaf et al., Applications of calixarenes in cancer chemotherapy: facts and perspectives, Drug Des., Dev. and Ther., 9:2831-2838 (2015).
Zhang et al., Preparation and size control of sub-100 nm pure nanodrugs, Nano Lett., 15(1):313-318 (2015).
Zhao et al., Nanodrug Formed by Coassembly of Dual Anticancer Drugs to Inhibit Cancer Cell Drug Resistance, ACS Appl. Mater. Interfaces., 7(34):19295-19305 (2015).
Zhao et al., Preparation and Characterization of Amphiphilic Calixarene Nanoparticles as Delivery Carriers for Paclitaxel, Chem. Pharm. Bull., 63:181-183 (2015).

(Continued)

*Primary Examiner* — James W Rogers
(74) *Attorney, Agent, or Firm* — MARSHALL, GERSTEIN & BORUN LLP

(57) ABSTRACT

Described herein are materials and methods for inducing therapeutic hypothermia in a subject in need thereof.

6 Claims, 15 Drawing Sheets

(56) References Cited

OTHER PUBLICATIONS

Zhao et al., Versatile Roles of Intracellularly Located TRPV1 Channel, J. Cell Physiol., 232(8):1957-1965 (2017).
Zhu et al., Therapeutic hypothermia versus normothermia in adult patients with traumatic brain injury: a meta-analysis, Spr.Plus., 5(1):801 (2016).
Agrawal et al., Nose-to-brain drug delivery: An update on clinical challenges and progress towards approval of anti-Alzheimer drugs, J. Control. Release, 281:139-177 (2018).
Ahmed et al., Hypothermia in Traumatic Brain Injury, Neurosurg. Clin. N. Am., 27(4):489-497 (2016).
Albanese et al., The Effect of Nanoparticle Size, Shape, and Surface Chemistry on Biological Systems, Ann. Rev. of Biom. Eng., 14:1-16 (2012).
Amidi et al., Preparation and characterization of protein-loaded N-trimethyl chitosan nanoparticles as nasal delivery system, J. of Controlled Release, 111:107-116 (2006).
Appendino et al., Development of the First Ultra-Potent "Capsaicinoid" Agonist at Transient Receptor Potential Vanilloid Type 1 (TRPV1) Channels and Its Therapeutic Potential, J. of Pharm. and Exp. Therapeutics, 312(2):561-570 (2005).
Arora et al., One-pot multicomponent click synthesis of pyrazole derivatives using cyclodextrin-supported capsaicin nanoparticles as catalyst, J. Mat. Sci., 52(19): 11413-11427 (2017).
Bharadwaj et al., Temporal assessment of nanoparticle accumulation after experimental brain injury: Effect of particle size, Sci. Rep., 6:29988 (2016).
Chan et al., Production methods for nanodrug particles using the bottom-up approach, Adv. Drug Deliv. Rev., 63(6):406-416 (2011).
Chen et al., An imagable and photothermal "Abraxane-like" nanodrug for combination cancer therapy to treat subcutaneous and metastatic breast tumors, Adv. Mater., 27(5):903-910 (2015).
Chen et al., Calixarene-Mediated Synthesis of Cobalt Nanoparticles: An Accretion Model for Separate Control over Nucleation and Growth, Chem. Mat., 26(2):941-950 (2014).
Chen et al., Drug-Induced Self-Assembly of Modified Albumins as Nano-theranostics for Tumor-Targeted Combination Therapy, ACS Nano, 9(5):5223-5233 (2015).
Davis et al., Absorption enhancers for nasal drug delivery, Cl. Pharmacokinetics, 42(13):1107-1128 (2003).
Diaz et al., Thermoregulation: Physiological and Clinical Considerations during Sedation and General Anesthesia, Anesthesia Prog., 57(1):25-33 (2010).
Dietrich et al., Hypothermic Treatment for Acute Spinal Cord Injury, Neurotherapeutics, 8:229-239 (2011).
Dietrich et al., Therapeutic hypothermia and targeted temperature management in traumatic brain injury: Clinical challenges for successful translation, Brain Res., 1640:94-103 (2016).
European Application No. 19861993, European Search Report and Opinion, dated May 17, 2022.
Feketa et al., Induction of therapeutic hypothermia by pharmacological modulation of temperature-sensitive TRP channels: theoretical framework and practical considerations, Temp. (Austin), 2(2):244-257 (2015).
Fosgerau et al., Drug-induced mild therapeutic hypothermia obtained by administration of a transient receptor potential vanilloid type 1 agonist, BMC Card. Dis., 10:51 (2010).
Gavva et al., The Vanilloid Receptor TRPV1 Is Tonically Activated In Vivo and Involved in Body Temperature Regulation, J. Neurosci., 27(13):3366-3374 (2007).
Grienberger et al., Imaging Calcium in Neurons, Neuron, 73(5):862-885 (2012).
Gu et al., Pharmacologically induced hypothermia attenuates traumatic brain injury in neonatal rats, Exp. Neurol., 267:135-142 (2015).
Guastella et al., Recommendations for the standardisation of oxytocin nasal administration and guidelines for its reporting in human research, Psychoneuroendocrinology, 38(5):612-625 (2013).
Hanson et al., Intranasal delivery bypasses the blood-brain barrier to target therapeutic agents to the central nervous system and treat neurodegenerative disease, BMC Neuroscience, 9:S5 (2008).
Horn et al., Organic Nanoparticles in the Aqueous Phase-Theory, Experiment, and Use, Angew. Chem. Int. Ed., 40(23):4330-4361 (2001).
Huang et al., Combination of small molecule prodrug and nanodrug delivery: amphiphilic drug-drug conjugate for cancer therapy, J. Am. Chem. Soc., 136(33):11748-11756 (2014).
International Application No. PCT/US2019/51938, International Preliminary Report on Patentability, dated Apr. 1, 2021.
International Application No. PCT/US2019/51938, International Search Report and Written Opinion, dated Jan. 30, 2020.
Iohara et al., Formation of stable hydrophilic C60 nanoparticles by 2-hydroxypropyl-ß-cyclodextrin, Mol. Pharm., 8(4):1276-1284 (2011).
Johansen et al., Drug-induced hypothermia as beneficial treatment before and after cerebral ischemia, Pathobiol., 81(1):42-52 (2014).
Kabadi et al., Fluid-percussion-induced traumatic brain injury model in rats, Nature protocols, 5:1552-1563 (2010).
Kasai et al., Creation of pure nanodrugs and their anticancer properties, Angnv. Chemie Int. Ed., 51(41):10315-10318 (2012).
Kongor et al., Calix-Based Nanoparticles: A Review, Top. Curr. Chem., 374(3): 28 (2016).
Kongor et al., Calix-Based Nanoparticles: A Review, Topics in Current Chemistry, 374(3):28 (2016).
Kulkarni et al., Nanotechnology-mediated nose to brain drug delivery for Parkinson's disease: a mini review, J. Drug Targ., 23(9):775-788 (2015).
Latorre et al., Cannabis, Cannabinoids, and Cerebral Metabolism: Potential Applications in Stroke and Disorders of the Central Nervous System, Curr. Cardi. Rep., 17:72 (2015).
Lee et al., Therapeutic Effects of Pharmacologically Induced Hypothermia against Traumatic Brain Injury in Mice, J. Neurotrauma, 31(6):1417-1430 (2014).
Li et al., Processable aqueous dispersions of graphene nanosheets, Nature Nanot., 3:101-105 (2008).
Li et al., Self-Assembled Chlorin e6 Conjugated Chondroitin Sulfate Nanodrug for Photodynamic Therapy, Biomacromolecules, 12(5):1724-1730 (2011).
Liu et al., Pharmacological hypothermia: a potential for future stroke therapy?, Neurol. Res., 38(6):478-490 (2016).
Marion et al., Current and Future Role of Therapeutic Hypothermia, J. Neurotrauma., 26(3):455-467 (2009).
Marzo et al., A Structure/Activity Relationship Study on Arvanil, an Endocannabinoid and Vanilloid Hybrid, J. Pharmacol. Exp. Ther., 300(3):984-991 (2002).
Merisko-Liversidge et al., Nanosizing for oral and parenteral drug delivery: A perspective on formulating poorly-water soluble compounds using wet media milling technology, Adv. Drug Deliv. Rev., 63(6):427-440 (2011).
Nakanishi et al., Reprecipitation Method for Organic Nanocrystals, Single Organic Nanoparticles, 17-31 (2003).
Nakatsuji et al., Thermosensitive Ion Channel Activation in Single Neuronal Cells by Using Surface-Engineered Plasmonic Nanoparticles, Angew. Chem. Int. Ed. Engl., 54(40):11725-11729 (2015).
Ozcan et al., Preparation and application of calix[4]arene-grafted magnetite nanoparticles for removal of dichromate anions, Mat. Sci. and Eng. C. Elesr. Sci., 29(8):2378-2383 (2009).
Raisinghani et al., Activation of transient receptor potential vanilloid 1 (TRPV1) by resiniferatoxin, J. Physiology, 567(3):771-786 (2005).
Romanovsky et al., The Transient Receptor Potential Vanilloid-1 Channel in Thermoregulation: A Thermosensor It Is Not, Pharmacol. Rev., 61(3):228-261 (2009).
Sagalyn et al., Therapeutic hypothermia after cardiac arrest in clinical practice: Review and compilation of recent experiences, Crit. Care Med., 37(7):S223-S226 (2009).
Sakurai et al., Mild Hyperthermia Worsens the Neuropathological Damage Associated with Mild Traumatic Brain Injury in Rats, Journal of Neurotrauma, 29(2):313-321 (2012).

(56) References Cited

OTHER PUBLICATIONS

Salatin et al., Effect of the surface modification, size, and shape on cellular uptake of nanoparticles, Cell Biol. Int., 39(8):881-890 (2015).

* cited by examiner

Figure 1J

MATERIALS AND METHODS FOR INDUCING THERAPEUTIC HYPOTHERMIA IN A MAMMALIAN SUBJECT

TECHNICAL FIELD

The present application is directed to nanoparticles comprising a vanilloid compound and the use of such nanoparticles to induce therapeutic hypothermia in a subject in need thereof.

BACKGROUND

Neurological disorders caused by cardiac arrest, brain trauma, spinal cord injury, hemorrhagic stroke, and other acute conditions are considered a major medical concern.(2, 18) Therapeutic hypothermia (TH), a type of target temperature management, has emerged as a beneficial post-traumatic treatment for such medical conditions.(8, 19-20) The basis of this therapy lies in intentionally decreasing the body temperature a couple of degrees below physiological temperature, 36° C., to prevent a surge in neuronal cell death.(19) TH can also positively impact cellular mechanisms, including decreasing/inhibiting free radical generation, inflammation, and processes such as angiogenesis and apoptosis.(8)

To date, several preclinical studies have shown long-term health improvement as a result of the application of moderate hypothermia to patients suffering from an ischemic or traumatic incident.(4) However, to achieve true efficient hypothermia, there are a series of factors that require better control. Those factors include the therapeutic window, optimal duration of cooling, and rewarming rate.(21) Current medical practices such as the use of ice packs, cooling blankets, or the injection of cold saline solutions lack the effectiveness to reach the target temperature at an adequate cooling speed.(4) In addition, the external cooling techniques are associated with side effects, such as shivering, and require a cumbersome operation setup.(22-23) The introduction of pharmacological agents that can induce targeted therapeutic hypothermia has emerged as the state-of-the-art treatment to provide neuroprotection.(4, 8, 24) However, the use of these agents, at the micro- and meso-scales, is still associated with several drawbacks, such as the use of high doses of the drugs/agents, the intravenous route of administration, and multiple side effects associated with TH treatment.(8) Vanilloids agents in particular such as capsaicin and rinvanil have shown specific and effective neuroprotective effects against traumatic conditions; (8) however, the continuous infusion method of high dose of these drugs has been associated with issues such as hypotension and bradycardia.(13) Thus, there remains a need in the art for a method of inducing therapeutic hypothermia that does not show adverse effects.

SUMMARY

The disclosure provides a method of making a nanoparticle comprising a vanilloid compound, the method comprising combining a vanilloid compound in a first solvent with an ion complexation agent selected from the group consisting of calixarenes, crown ethers and calixcrowns in a second solvent to produce an admixture in aqueous suspension; and sonicating the suspension for a time sufficient to produce a nanoparticle comprising the vanilloid compound and the complexation agent, wherein the nanoparticle has a particle size ranging from 4 nm to 100 nm. In some embodiments, the ion complexation agent is 4-tert-butylcalix[4]arene.

In another aspect, the disclosure also provides a method of inducing hypothermia in a subject in need thereof comprising administering to the subject a composition comprising a nanoparticle comprising a vanilloid compound and an ion complexation agent and having a particle size ranging from 4 nm to 100 nm in an amount effective to induce hypothermia in the subject. The sonicating step can be done by any known method. In some embodiments, the sonicating step is performed by bath sonication or probe sonication.

In some embodiments, the first solvent and the second solvent are miscible. In some embodiments, the first solvent comprises an alcohol (e.g., ethanol). In some embodiments, the second solvent comprises chloroform.

In some embodiments, the vanilloid compound is capsaicin, nonivamide, arvanil, rinvanil or resiniferatoxin.

In some embodiments, the ion complexation agent is 4-tert-butylcalix[4]arene.

The disclosure also provides an aqueous suspension comprising a nanoparticle comprising a vanilloid compound and an ion complexation agent, wherein the nanoparticle has a particle size ranging from 4 nm to 100 nm, wherein the nanoparticle remains in suspension for at least one week when stored at 25° C. In some embodiments, the nanoparticle remains in suspension for at least 25 weeks when stored at 25° C.

BRIEF DESCRIPTION OF THE FIGURES

Figure 1J:
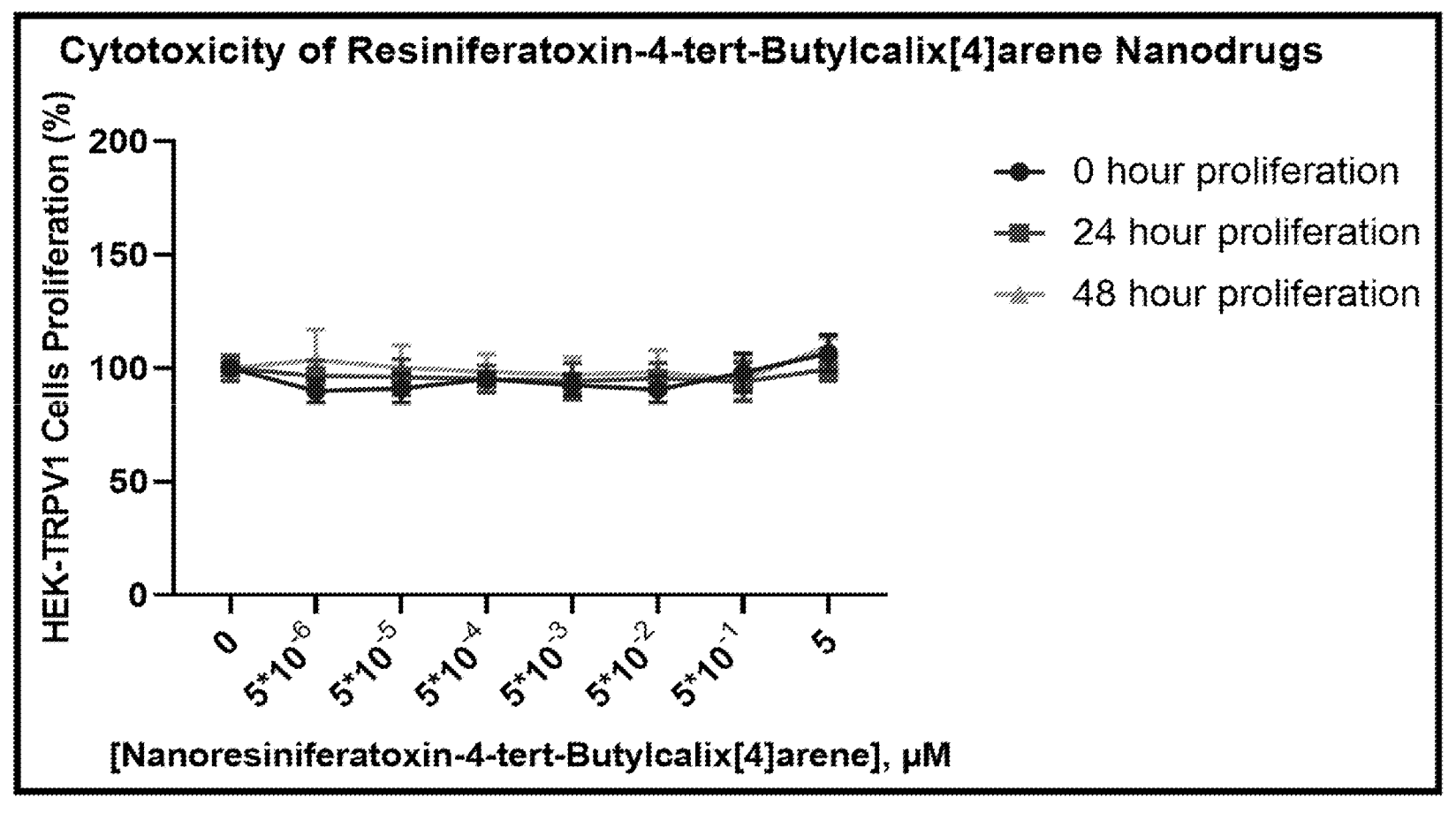

FIGS. 1F-1J are graphs demonstrating that none of the nanoparticles comprising capsaicin-4-tert-butylcalix[4]arene (FIG. 1F), nonivamide-4-tert-butylcalix[4] arene (FIG. 1G), arvanil-tert-butylcalix[4] arene (FIG. 1H), rinvanil-4-tert-butylcalix[4]arene (FIG. 1I), and RTX and 4-tert-butylcalix[4]arene (FIG. 1J) inhibited the proliferation of TRPV1-overexpressed HEK293 cells for a period of 48 hours. X-axis: concentration of nanoparticle; Y-axis: percent cell proliferation.

FIG. 2 is a graph showing the presence of rinvanil nanoparticles (nanorinvanil) caused calcium influx upon activation of TRPV1 receptors, which was translated by an increase of fluorescence intensity in comparison to the control (rinvanil in non-nanoparticle form ("bulk").

FIG. 3A is a graph showing the results of brain and body temperature monitoring after nasal administration of nanorinvanil (0.05 mg/kg) in rats over time. X-axis: time (minutes); Y-axis: temperature (° C.). FIG. 3B is a graph showing the results of mean arterial pressure monitoring after administration of nanorinvanil (0.05 mg/kg) in rats over time. X-axis: time (minutes); Y-axis: mean blood pressure (mmHg). FIG. 3C is a graph showing the results of brain temperature change after nasal administration of nanorinvanil (0.05 mg/kg) in rats over time. X-axis: time (minutes); Y-axis: temperature difference ΔT (° C.).

DETAILED DESCRIPTION

Figure 1A:
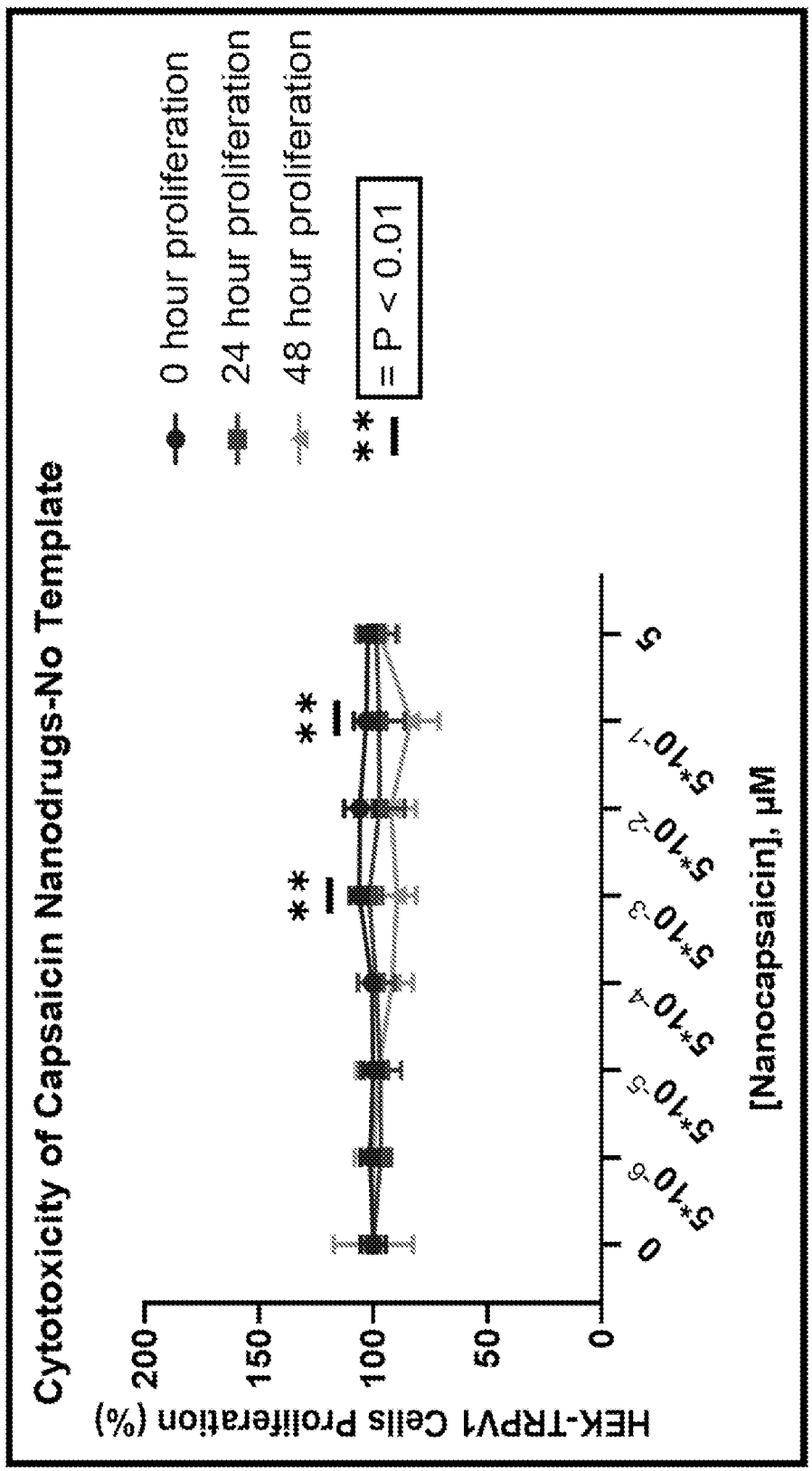
FIGS. 1A-1E are graphs demonstrating that nanoparticles comprising a vanilloid compound (capsaicin (FIG. 1A), nonivamide (FIG. 1B), arvanil (FIG. 1C), rinvanil (FIG. 1D), and resiniferatoxin (RTX) (FIG. 1E)) did not inhibit the proliferation of TRPV1-overexpressed HEK293 cells for a period of 48 hours. X-axis: concentration of nanoparticle; Y-axis: percent cell proliferation.
Figure 1B:
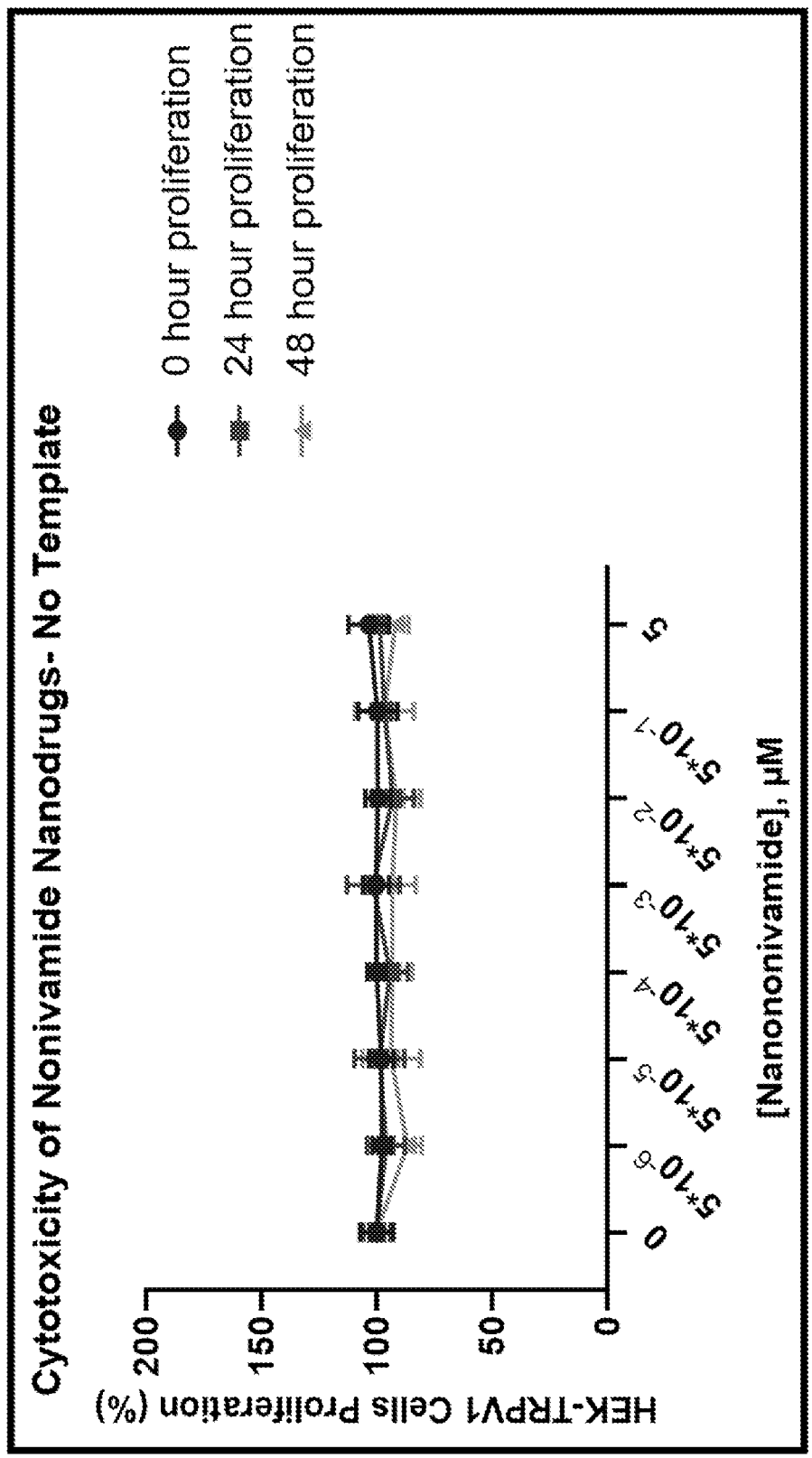
Figure 1C:
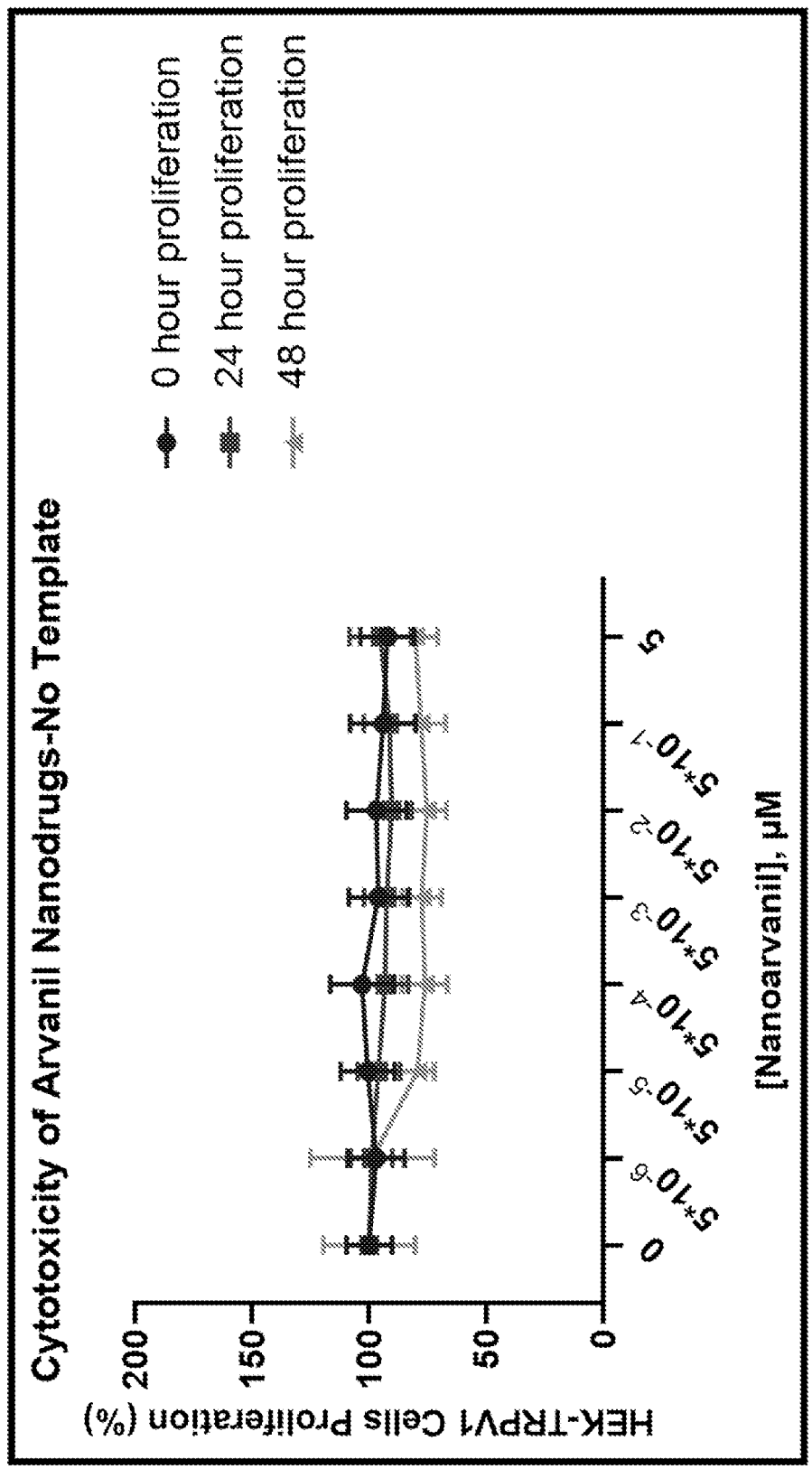
Figure 1D:
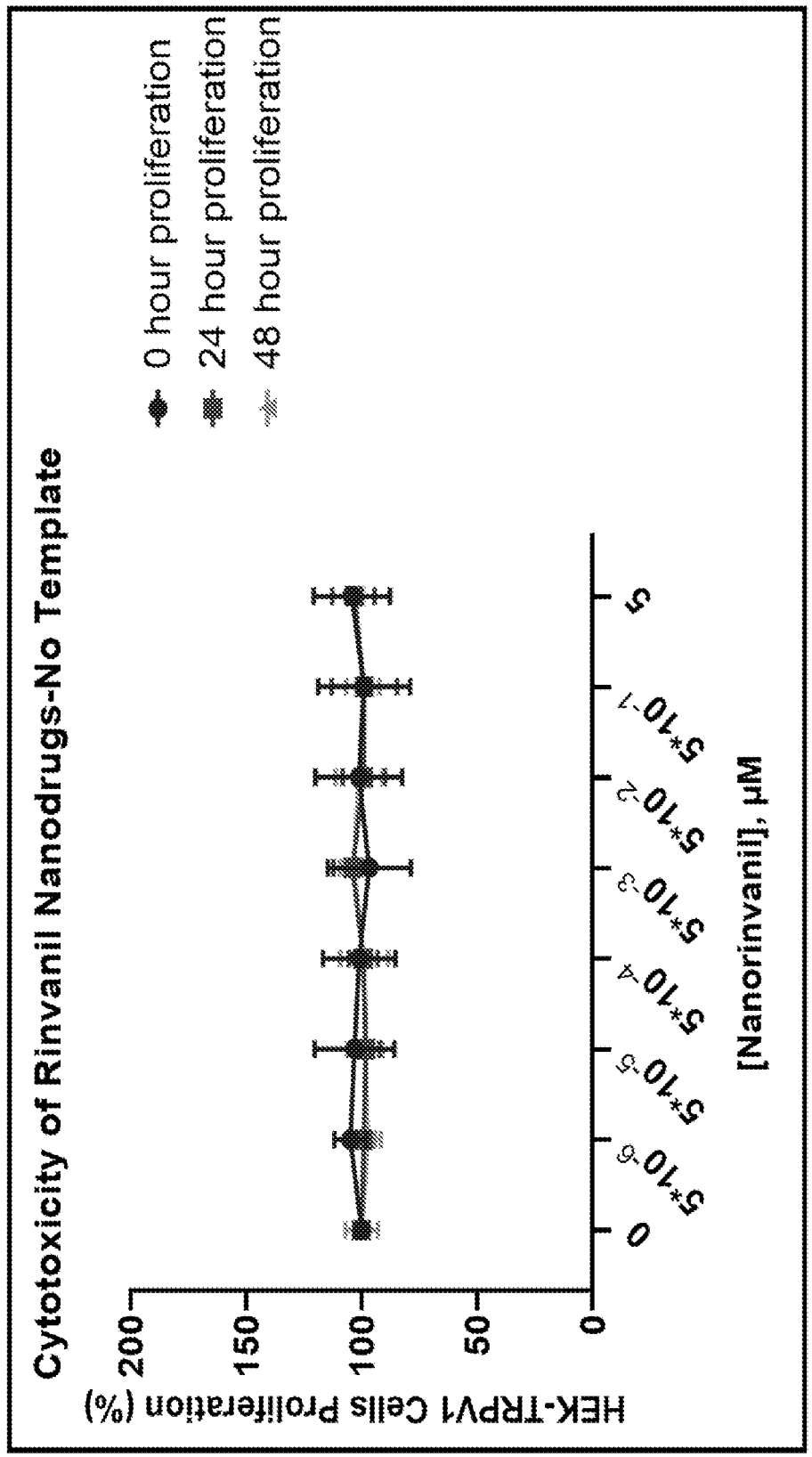
Figure 1E:
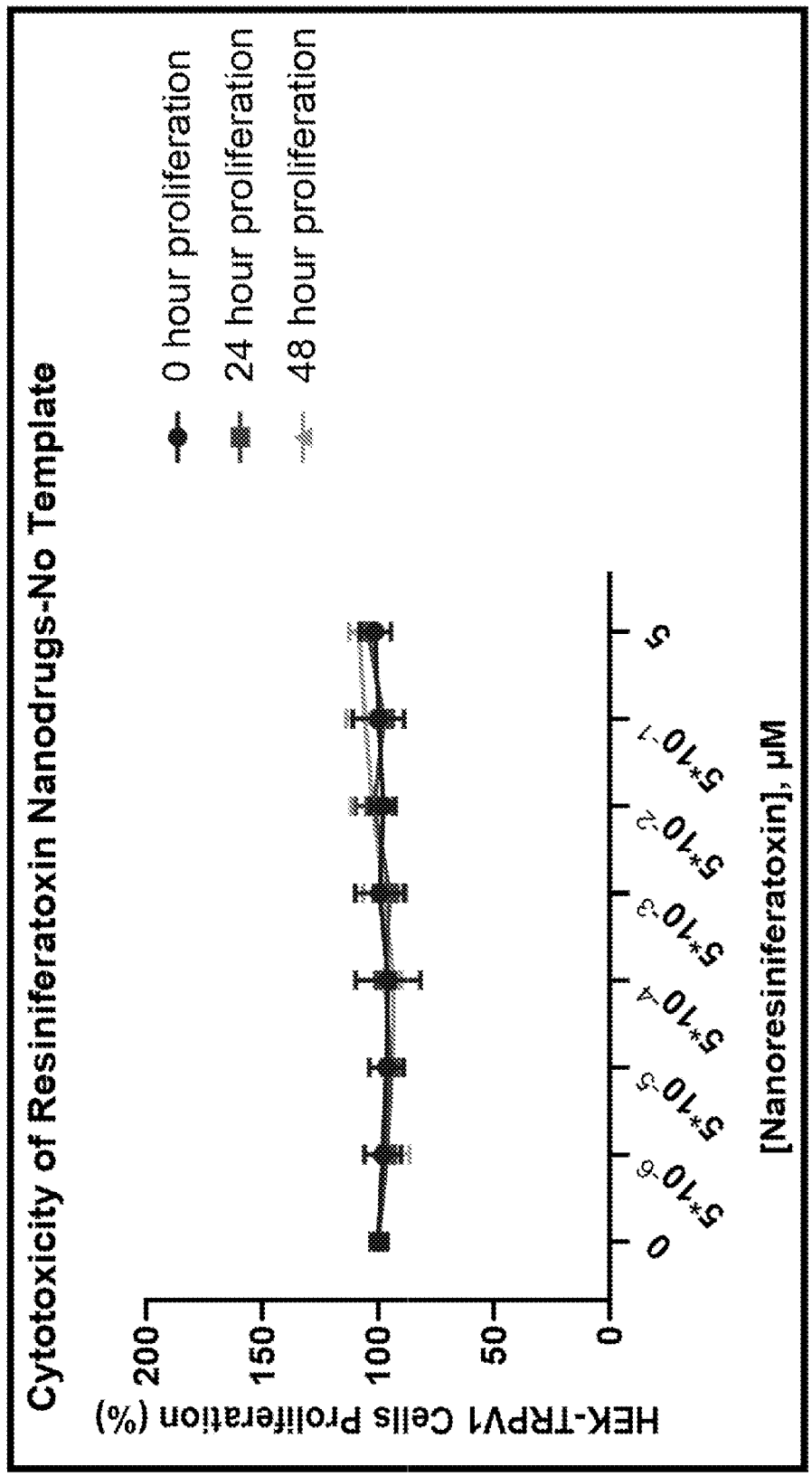
Figure 1F:
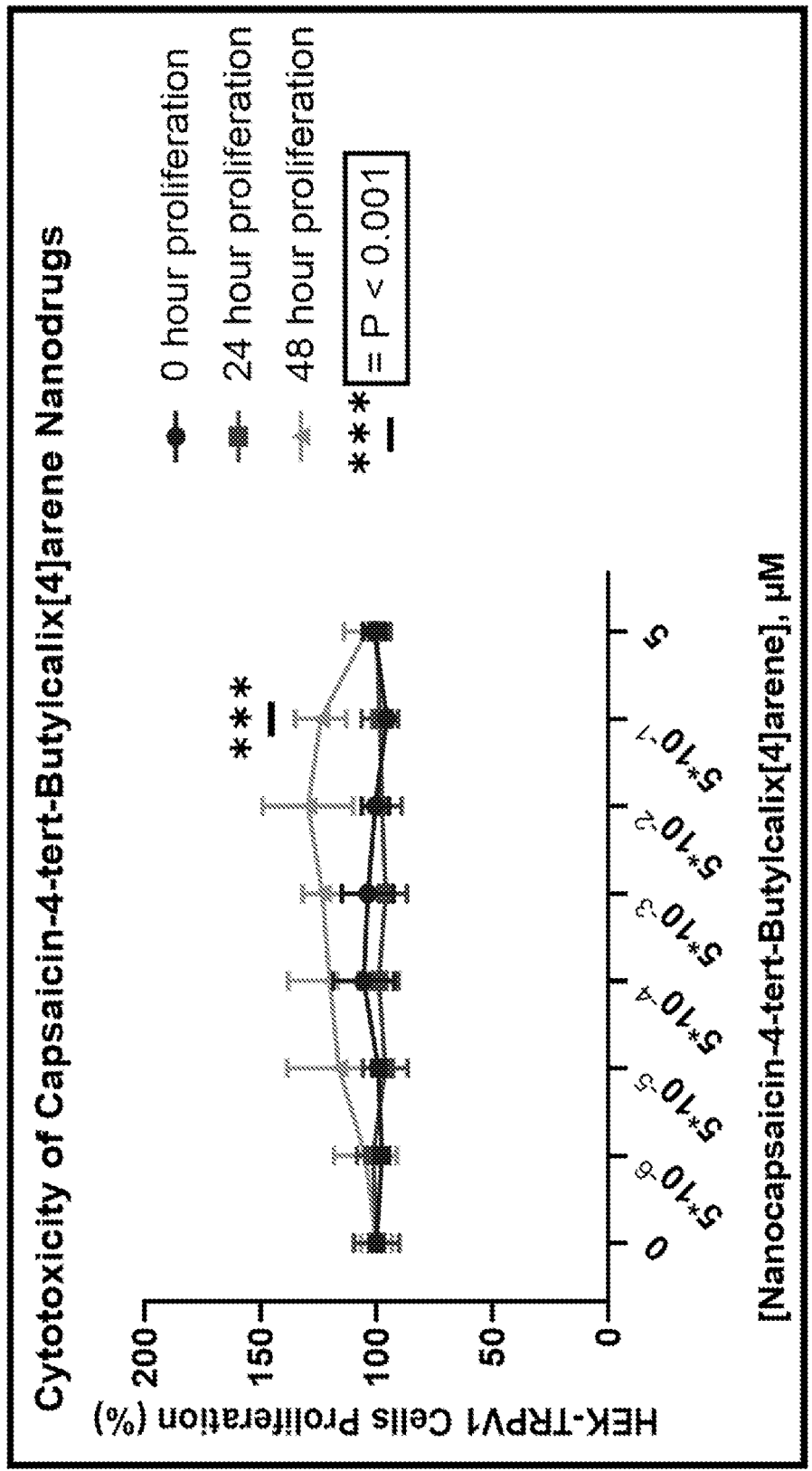
Figure 1G:
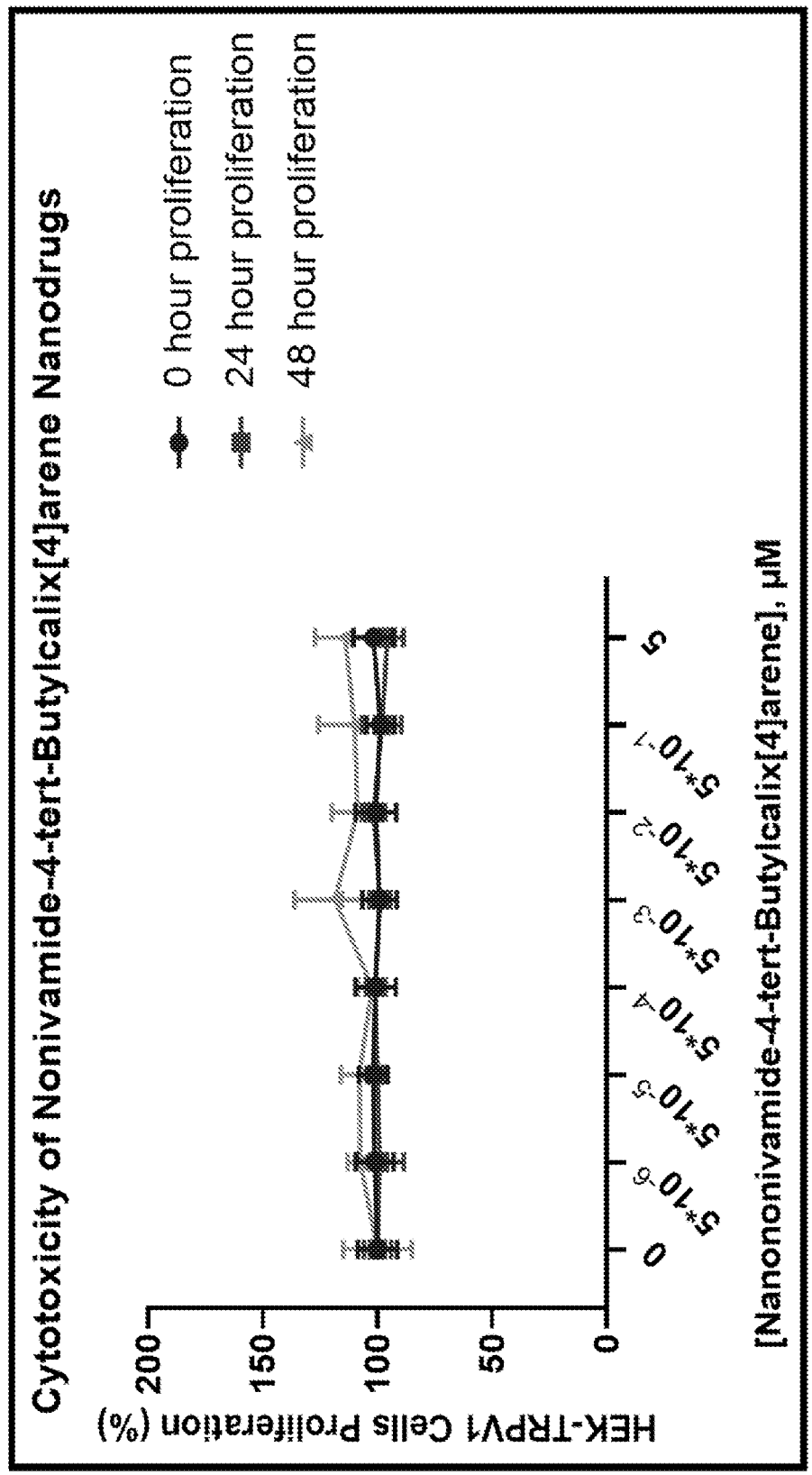
Figure 1H:
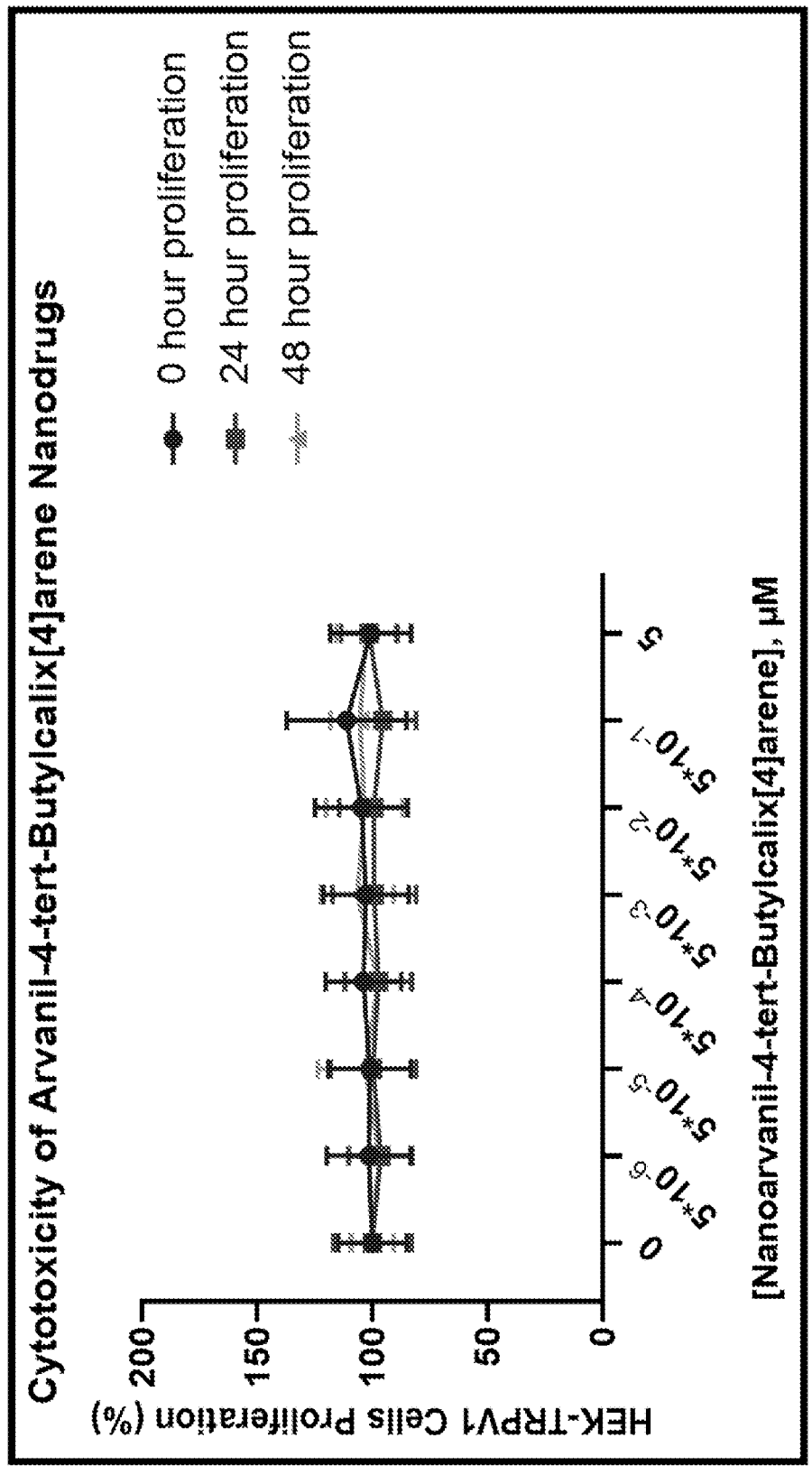
Figure 1I:
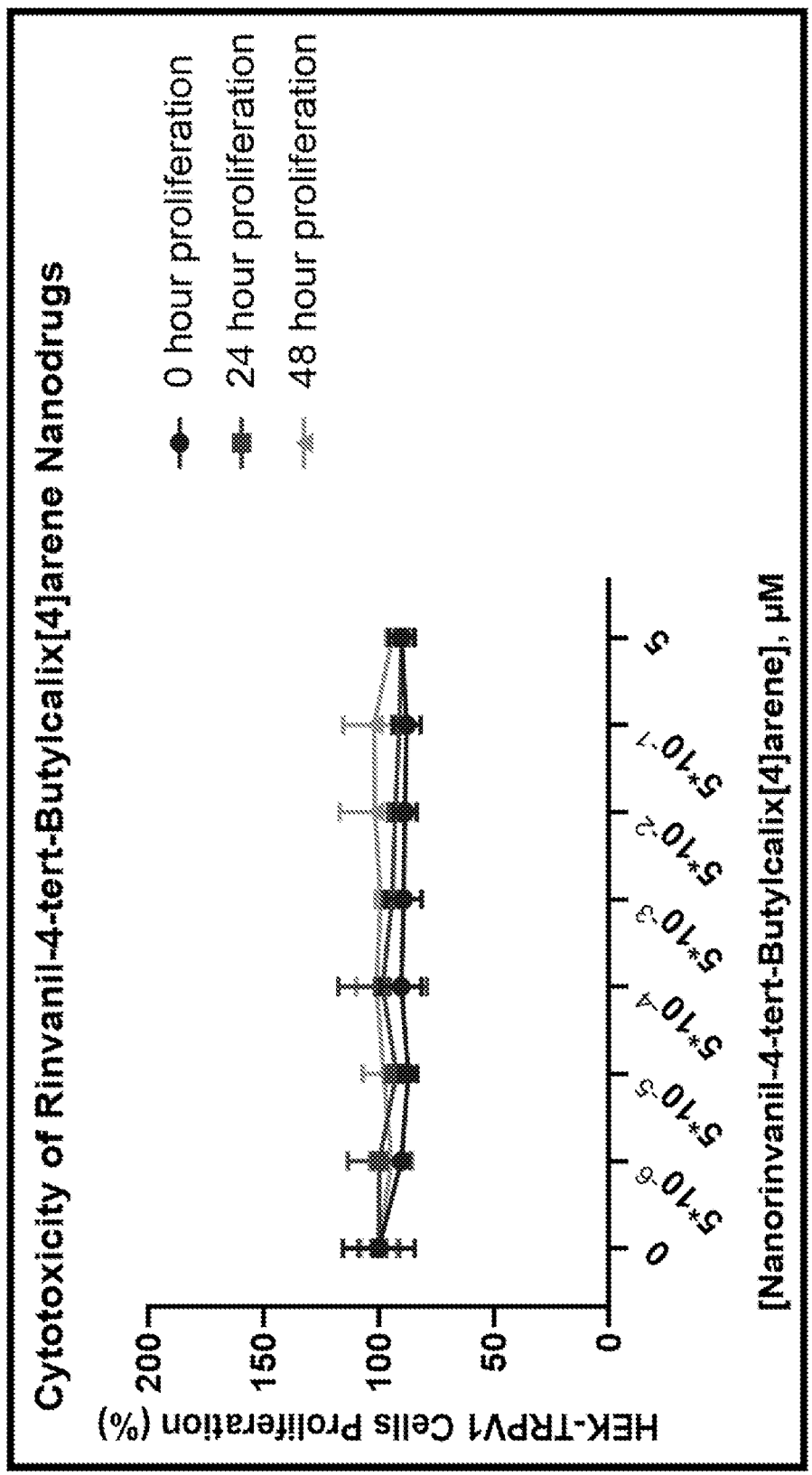
Figure 1K:
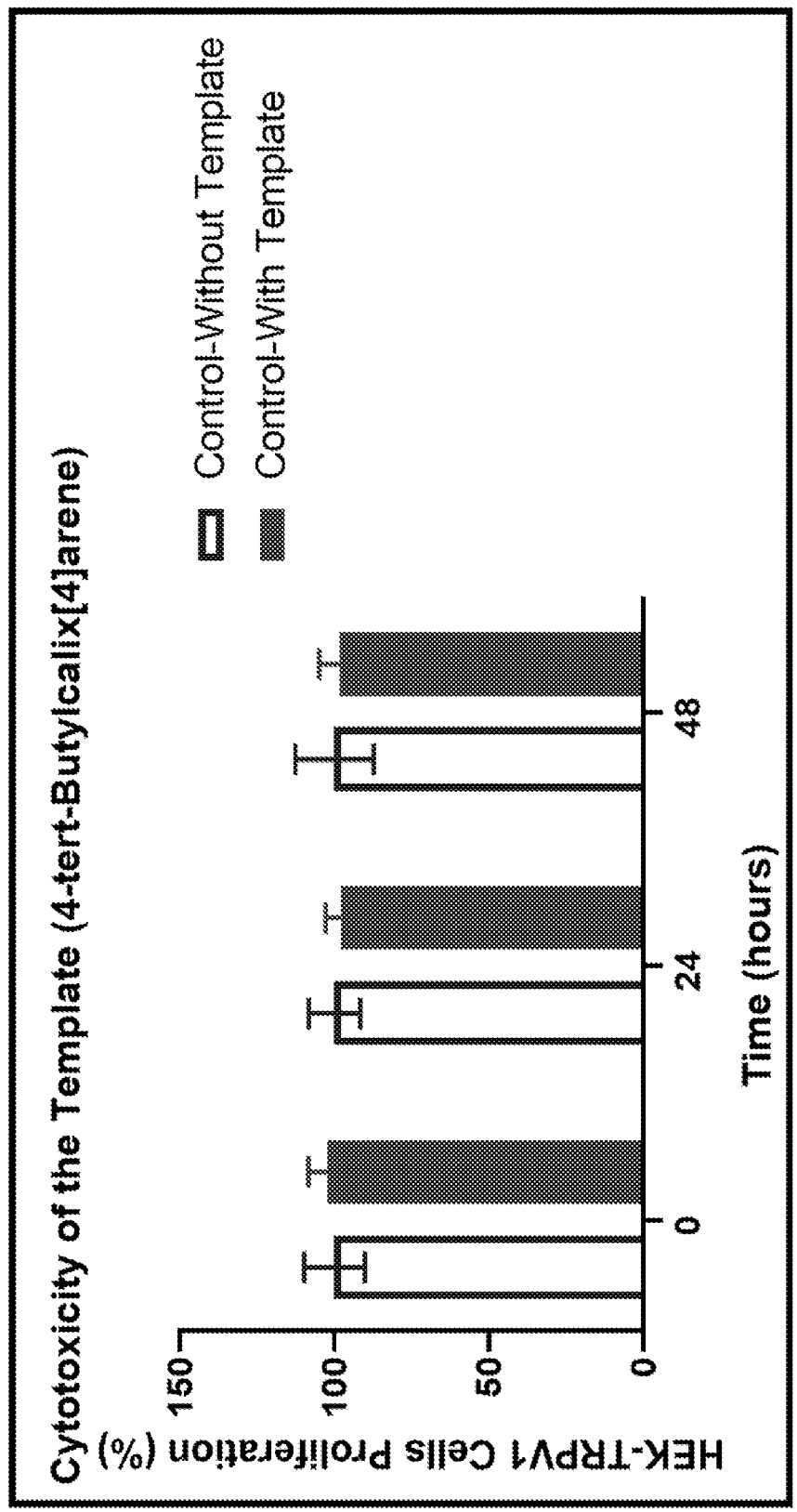
FIG. 1K is a graph comparing the cytotoxicity of the medium of suspension with (right column at each time point) or without (left column at each time point) the 4-tert-butylcalix[4]arene template. X-axis: time of incubation (hours); Y-axis: percent cell proliferation.

The present disclosure is based, at least in part, on the discovery that vanilloid compounds provided in a carrier-free nanoparticle form are capable of inducing therapeutic hypothermia (TH) in a non-invasive manner. Providing a vanilloid compound as a nanoparticle improves the properties of the compound in crossing the Blood Brain Barrier (BBB) and results in a more efficient therapeutic hypothermia intervention compared to standard of care vanilloid formulations administered via infusion. In this regard, the carrier-free vanilloid nanoparticles described herein (e.g., free of carriers such as polymers, liposomes, and dendrimers) will eliminate issues related to drug loading capacity and/or toxicity of such carriers. Furthermore, the process of making the nanoparticles with an ion complexation agent (such as 4-tert-butylcalix[4]arene) as described herein mediates the delivery of stable and efficient hydrophobic nanodrugs via a non-invasive intranasal formulation to induce therapeutic hypothermia. The nanoparticle formulations described herein addresses the concern of the poor water solubility of several efficient drugs that could be used as agents in therapeutic hypothermia and cannot be employed due to their lack of solubility.

Vanilloid Compounds

Vanilloid compounds are capable of chemically inducing hypothermia; however, the dissolution of these hydrophobic formulations requires the use of an organic solvent. (39) The transformation of the free molecules of vanilloid compounds into vanilloid nanoparticles under aqueous conditions circumvents the need for a toxic organic solvent.

Vanilloid compounds are capable of binding the Vanilloid Receptor 1 (VR1), also known as the Transient Receptor Potential Cation Channel, Subfamily V (TRPV1). The term vanilloid compound includes, but is not limited to, compounds such as capsaicin (C; 8-methyl-N-vallilyl-6-nonenamide), dihydrocapsaicin (DHC), nordihydro-capsaicin (NDHC), homodihydro-capsaicin (HDHC), homocapsaicin (HC), olvanil (N-9-Z-octadecenoyl-vanillamide), rinvanil (vanillamide of ricinoleic acid), arvanil (N-vanillylarachidonamide), PhAR (phenylacetylrinvanil), nuvanil, farvanil (vanillamide of farnesic acid), Ac-Rinvanil, retvanil (vanillamide of retinoic acid), nonivamide, ervanil (vanillamide of erucic acid), resiniferatoxin (RTX), and Zingerone.

Method of Making Vanilloid Nanoparticles

Most vanilloid compounds are hydrophobic, which means that dissolution of such compounds in an aqueous formulation requires the use of an organic solvent(39). Combining a vanilloid compound with an ion complexation agent under aqueous conditions to produce vanilloid nanoparticles circumvents the need for a toxic organic solvent. In some embodiments, the ion complexation agent is a calixarene, a crown ether, or a calixcrown. Exemplary ion complexation agents include, but are not limited to, 4-tert-butylcalix[4]arene, dibenzo-18-crown-6, and calixcrowns.

In this regard, described herein is a method of making a nanoparticle comprising a vanilloid compound, the method comprising combining a vanilloid compound in a first solvent with an ion complexation agent selected from the group consisting of a calixarene, a crown ether and a calixcrown in a second solvent to produce an admixture in aqueous suspension; and sonicating the suspension for a time sufficient to produce a nanoparticle comprising the vanilloid compound and the complexation agent, wherein the nanoparticle has a particle size ranging from 4 nm to 100 nm. In some embodiments, the ion complexation agent is 4-tert-butylcalix[4]arene, dibenzo-18-crown-6 or a calixcrown.

The sonicating step can be performed by any known method. In some embodiments, the sonicating step is performed by bath sonication or probe sonication. The sonicating step is performed for a time sufficient to produce a nanoparticle comprising the vanilloid compound and the ion complexation agent and having a particle size ranging from 4 nm to 100 nm. In some embodiments, the suspension is sonicated for at least 1 minute, at least 2 minutes, at least 3 minutes, at least 4 minutes, at least 5 minutes. In some embodiments, the suspension is sonicated for less than 10 minutes (e.g., 9 minutes, 8 minutes, 7 minutes, 6 minutes, 5 minutes, 4 minutes, 3 minutes, 2 minutes or 1 minute). In some embodiments, the suspension is sonicated for about 5 minutes.

The vanilloid compound is present in a first solvent. In some embodiments, the first solvent is miscible with water. In some embodiments, the first solvent comprises an alcohol (e.g., ethanol) or other organic solvent (e.g., acetonitrile or dimethylsulfoxide (DMSO)). In some embodiments, the first solvent comprises about 40% alcohol, about 50% alcohol, about 55% alcohol, about 60% alcohol, about 65% alcohol, about 70% alcohol, about 75% alcohol, about 80% alcohol, about 85% alcohol, about 90% alcohol or about 95% alcohol.

The ion-complexation agent is present in a second solvent. In some embodiments, the second solvent comprises chloroform or other organic solvent that is different than the first organic solvent (e.g., dichloromethane, for synthesis purposes only).

The first solvent and the second solvent are preferably miscible.

In some embodiments, the method produces a nanoparticle having a particle size ranging from 4 nm to 100 nm (e.g., about 50 nm to about 100 nm, or about 20 nm to about 100 nm, or about 20 nm to about 50 nm, or about 75 nm to about 100 nm, or about 4 nm to about 30 nm, or about 10 nm to about 50 nm). In some embodiments, the nanoparticle has a particle size of about 4 nm, about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm or about 100 nm.

Transmission electron microscopy (TEM) can provide information about the size, shape, and distribution of the nanoparticle population. Powder X-ray diffraction (XRD) patterns can provide the most complete information regarding the type and quality of the crystal or amorphous structure of the nanoparticle. Estimates of size are also possible since particle diameter is inversely related, via the X-ray coherence length, to the peak width. For example, the diameter of the nanoparticle can be measured directly by transmission electron microscopy or estimated from X-ray diffraction data using, for example, the Scherrer equation. The aggregation state can also can be estimated from the UV/Vis absorption spectrum.

Treatment Methods

Also described herein is a method of inducing therapeutic hypothermia in a subject in need thereof comprising administering to the subject a vanilloid compound and an ion complexation agent and having a particle size ranging from 4 nm to 100 nm, in an amount effective to induce hypothermia in the subject. Hypothermia is the lowering of the core temperature of the body below normal level. Normal body temperature in an adult human measured rectally over 24 hours is 37° C.±0.6° C. and is thus variable between individuals, and over time within the individual. Hypothermia as a medical condition is usually defined as the effects seen on the body once the core temperature drops below 35° C. It may become critical, if the body temperature falls below 32° C. The phrase "inducing hypothermia" or "inducing therapeutic hypothermia" as used herein is defined as the lowering of the core body temperature of a subject below normal levels. In other words, any temperature below the normal core body temperature of the specific individual with its natural variations at the given point in time of the day, or period, herein is defined as being hypothermic. In particular, hypothermia is a temperature below 35.5° C. (e.g., below 35.0° C., below 34.5° C., or below 34.0° C.).

In some embodiments, the nanoparticle induces hypothermia in the subject to any range of temperatures between 37° C. and 31° C. (e.g., between 36.5° C. and 31.5° C., between 36° C. and 32° C., between 35.5° C. and 32.5° C., between 35° C. and 33° C., or between 34.5° C. and 33.5° C.). In some embodiments, the nanoparticle induces hypothermia in the subject to any range of temperatures between 37° C. and 34° C., such as between 36.5° C. and 34.5° C., such as 36° C. and 35° C., alternatively between 34° C. and 31° C., such as between 33.5° C. and 31.5° C., such as 33° C. and 32° C., alternatively between 36° C. and 33° C. or 35° C. and 32° C. In some embodiments, a nanoparticle described herein induces hypothermia in the range of between 36° C. to 32° C., or between 35° C. and 33° C., or 34° C. and 32° C.

In some embodiments, a nanoparticle described herein induces hypothermia in a subject in need thereof to a specific temperature such as 37° C., 36.5° C., 36° C., 35.5° C., 35° C., 34.5° C., 34° C., 33.5° C., 33° C., 32.5° C., 32° C., 31.5° C. or 31° C. In some embodiments, a nanoparticle described herein induces hypothermia to any of the above specific temperatures within a range of ±0.5° C., the range thus being between ±0.4° C., such as between ±−0.3° C., such as between ±0.2° C., or such as between ±0.1° C.

Body temperature may be measured by a variety of means by mercury, electronic or plastic strip thermometers on different areas of the body such as the forehead, mouth, armpit, ear or rectum. The temperature referred to in the present application is the core body temperature. Some of the above methods of measurement will indicate a different temperature than the core temperature, but are still useful in the context of the disclosure.

In some embodiments, the induction of hypothermia in the subject follows a predictable course and is responsive to the dose of the nanoparticle. The induction of the hypothermic condition may be rapid or slow depending on the situation of the subject in need of treatment. Also depending on the severity of the condition to be treated, retaining the subject in the hypothermic state for variable durations of time is specifically contemplated. Reversing the hypothermic state of the subject in a controlled fashion either slowly or rapidly depending on the health status of the subject is also contemplated.

The nanoparticles described herein are administered intranasally. The administration of these nano-therapeutics via a nose to brain transport route will achieve a localized effect. (40) The induction of cooling via nasal spray delivers precise and accurate control over core body temperature resulting in rapid action and reaching the targeted temperature in a fast manner.(41-42) Intranasal delivery of nano-therapeutics will bypass the BBB and result in an efficient cooling effect, profiting from the high permeability and absorption surface, as well as the reduced enzyme activity of nasal fluids.(41-42). In some embodiments, the vanilloid nanoparticles described herein are formulated into a pharmaceutical composition to be administered as a nasal spray.

In some embodiments, the one or more doses of vanilloid nanoparticles can comprise less than 0.99 milligrams vanilloid nanoparticles per kilogram of body weight (mg/kg). For example, the dose of vanilloid nanoparticles may comprise at least about 0.001 mg/kg, 0.005 mg/kg, 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.25 mg/kg, about 0.26 mg/kg, about 0.27 mg/kg, about 0.28 mg/kg, about 0.29 mg/kg, about 0.3 mg/kg, about 0.31 mg/kg, about 0.32 mg/kg, about 0.33 mg/kg, about 0.34 mg/kg, about 0.35 mg/kg, about 0.36 mg/kg, about 0.37 mg/kg, about 0.38 mg/kg, about 0.39 mg/kg, about 0.4 mg/kg, about 0.41 mg/kg, about 0.42 mg/kg, about 0.43 mg/kg, about 0.44 mg/kg, about 0.45 mg/kg, about 0.46 mg/kg, about 0.47 mg/kg, about 0.48 mg/kg, or about 0.49 mg/kg, or about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 0.96 mg/kg, about 0.97 mg/kg, about 0.98 mg/kg or about 0.99 mg/kg. Ranges between any and all of these endpoints are also contemplated, e.g., about 0.01 mg/kg to about 0.5 mg/kg, about 0.5 mg/kg to about 0.99 mg/kg, about 0.1 mg/kg to about 0.3 mg/kg, about 0.3 mg/kg to about 0.8 mg/kg, about 0.01 mg/kg to about 0.99 mg/kg, about 0.2 mg/kg to about 0.4 mg/kg, about 0.05 mg/kg to about 0.5 mg/kg, or about 0.05 mg/kg to about 0.2 mg/kg.

Selection of the additional formulation materials may be driven by, for example, the intended route of administration, delivery format and desired dosage. See, for example, REMINGTON'S PHARMACEUTICAL SCIENCES, supra. The primary vehicle or carrier in a pharmaceutical composition is aqueous in nature. For example, a suitable vehicle or carrier may be water for injection, physiological saline solution, possibly supplemented with other materials common in compositions for intranasal administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments, the composition may be prepared for storage by mixing the selected composition having the desired degree of purity with optional formulation agents (REMINGTON'S PHARMACEUTICAL SCIENCES, supra) in the form of a lyophilized cake or an aqueous solution.

Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

Stability

The terms "stability" and "stable" as used herein refer to the resistance of the nanoparticles in the composition to fall out of suspension under given manufacture, preparation, transportation and/or storage conditions. Nanoparticle formulations comprising a high degree of stability demonstrate enhanced reliability and safety and, as such, are advantageous for clinical use.

Nanoparticle stability in a composition is optionally assessed by examining a desired parameter of the nanoparticle in the composition (e.g., falling out of suspension, etc.) over time. In this regard, a parameter is typically examined at an initial time point (T0) and an assessment time point (T1), optionally while exposing the composition to any of a number of environmental conditions, and compared. An initial time point can be, for instance, the time that the nanoparticle is first formulated in the suspension or first examined for quality (i.e., examined to determine whether the composition meets regulatory or manufacturing specifications with respect to remaining in suspension). An initial time point also can be the time at which the nanoparticle is reformulated in a composition (e.g., reformulated at a higher or lower concentration compared to an initial preparation). An assessment time point is, in various embodiments, about 1 week (or about 2 weeks, or about 3 weeks, or about 4 weeks, or about 5 weeks, or about 6 weeks, or about 7 weeks, or about 8 weeks, or about 10 weeks, or about 3 months, or about 6 months or about 1 year) after the initial time point. The desired parameter (e.g., remaining in suspension) of the nanoparticles in the composition can be assessed under a variety of storage conditions, such as temperatures of −30° C., 4° C., 20° C. or 40° C., shaking, pH, storage in different container materials (e.g., glass vials, pre-filled syringes, etc.), and the like.

In various embodiments, less than 5% of the nanoparticles described herein in the composition fall out of suspension under conditions of interest. For instance, less than 4%, or less than 3%, or less than 2%, or less than 1% of the nanoparticles described herein fall out of suspension after storage at −30° C., 4° C., 20° C., 25° C. or 40° C. for a period of about 1 week (or about 2 weeks, or about 3 weeks, or about 4 weeks, or about 5 weeks, or about 6 weeks, or about 7 weeks, or about 8 weeks, or about 10 weeks, about 11 weeks, or about 12 weeks (or about 3 months), or about 13 weeks, about 14 weeks, about 15 weeks, about 16 weeks (or about 4 months) or about 17 weeks, or about 18 weeks, or about 19 weeks, or about 20 weeks (or about 5 months), or about 21 weeks, or about 22 weeks, or about 23 weeks, or about 24 weeks (or about 6 months), or about 25 weeks, or about 26 weeks, or about 27 weeks, or about 28 weeks, or about 1 year). In some embodiments, less than 5% (or less than 4% or less than 3% or less than 2% or less than 1% or less) of the nanoparticles described herein fall out of suspension after storage for two weeks at about 4° C. In some embodiments, the nanoparticles in the composition remain in suspension for at least one week when stored at 25° C. In some embodiments, the nanoparticles in the composition remain in suspension for at least twenty-five weeks when stored at 25° C.

For example at least 85% (or at least 90%, or at least 91%, or at least 92%, or at least 93%, or at least 94%, or at least 95%, or at least 96%, or at least 97%, or at least 98%, or at least 99%) of the nanoparticles in the composition optionally remain in suspension after storage at −30° C., 4° C., 25° C. or 40° C. for a period of about 1 week (or about 2 weeks, or about 3 weeks, or about 4 weeks, or about 5 weeks, or about 6 weeks, or about 7 weeks, or about 8 weeks, or about 10 weeks, or about 3 months, or about 6 months or about 1 year). In some embodiments, at least 85% (or at least 90%, or at least 91%, or at least 92%, or at least 93%, or at least 94%, or at least 95%, or at least 96%, or at least 97%, or at least 98%, or at least 99% or more) of the nanoparticles present in the composition remain in suspension after two weeks of storage at about 4° C. In some embodiments, at least 99% of the nanoparticles in the composition remain in suspension after storage for two weeks at about 4° C. for two weeks and/or at least 95% of the nanoparticles present in the composition remain in suspension after storage for two weeks at 40° C. and/or at least 95% of the nanoparticles present in the composition remain in suspension after storage for two weeks at 25° C.

Maintaining the functionality/activity of the nanoparticles in the composition is also contemplated herein. Assays for detecting and/or quantifying the functionality/activity of the nanoparticles can be assessed, for example, as described in Example 3. Optionally, the nanoparticles demonstrate about 50-100% activity under conditions of interest compared to the activity of the nanoparticles at the initial time point. For example, the nanoparticles retain a level of activity of between about 60-90% or 70-80% compared to the activity the initial time point. Accordingly, functional activity of the nanoparticles includes improvement of activity/functionality of at least about 50%, about 55%, about 60%, about 65%, about 70%, about 75%, about 80%, about 85%, about 90%, about 95% or 100% and can include activity measurements greater than 100% such as 105%, 110%, 115%, 120%, 125% or 150% or more compared to the activity of a vanilloid compound formulation in the absence of nanoparticles (Example 3).

EXAMPLES

Example 1—Synthesis of Vanilloid Nanoparticles

A volume of 75-100 μL of a vanilloid compound (i.e., capsaicin, nonivamide (pseudocapsaicin), arvanil, rinvanil, or resiniferatoxin (RTX)) (1 mM-4 mM in ethanolic solution) was added dropwise to 5 mL of deionized and distilled water in a vial under sonication. In instances where a template was used, a volume of 10 μl (or 20 μl) of calixarene-based compound (4-tert-Butylcalix[4]arene) (3 mM solution in chloroform) was then added. The mixture was sonicated 5 minutes using a bath sonicator. The vial was covered with punctured parafilm and left for 24 hours to allow for the evaporation of the ethanol (and chloroform in cases where the template is used) from the mixture before characterization of the resulting nanoparticles.

According to transmission electron micrograph (TEMs) analysis, the average size of the resulting capsaicin, nonivamide (pseudocapsaicin), arvanil, rinvanil, and resiniferatoxin nanoparticles after bath sonication synthesis in presence of 10 μL, (or 20 μL) calixarene-based compound (4-tert-Butylcalix[4]arene) were 111±28 nm, 4±1 nm, 29±5 nm (90±20 nm for the larger nanoparticles), 221±44 nm and 53±9 nm, respectively. Dynamic light scattering (DLS) and zeta potential of the drug nanoparticles was also assessed and the results are shown below in Table 1.

| Drug Nanoparticle | DLS (per intensity; 90° scattering) - with 10 μl calixarene derivative | Zeta potential- with 10 μl calixarene derivative | DLS (per intensity; 90° scattering) - with 20 μl calixarene derivative | Zeta potential- with 20 μl calixarene derivative |
|---|---|---|---|---|
| Capsaicin | 78 ± 34 nm and larger size of 323 ± 145 nm | −23.0 ± 1.4 mV (pH 3.4) | 235 ± 24 nm | −22.5 ± 2.8 mV (pH: 2.8-3.2) |

-continued

| Drug Nanoparticle | DLS (per intensity; 90° scattering) - with 10 μl calixarene derivative | Zeta potential- with 10 μl calixarene derivative | DLS (per intensity; 90° scattering) - with 20 μl calixarene derivative | Zeta potential- with 20 μl calixarene derivative |
|---|---|---|---|---|
| Nonivamide | 74 ± 11 nm and larger size of 385 ± 132 nm | −20.2 ± 2.9 mV (pH 3.7) | 241 ± 35 nm | −21.0 ± 3.5 mV (pH: 2.9-3.2) |
| Arvanil | 304 ± 44 nm and presence of smaller size around 73 ± 20 nm | −42.7 ± 9.3 mV (pH: 5.4-7.3) | 313 ± 8 nm | −43.0 ± 2.8 mV (pH: 5.4-7.9) |
| Rinvanil | 237 ± 29 nm | −44.5 ± 11.9 mV (pH: 7.3-7.4) | 128 ± 25 nm | −24.4 ± 5.0 mV (pH: 3.3-3.4) |
| Resiniferatoxin | 188 ± 21 nm | −11.7 ± 4.1 mV (pH 2.9-3.6) | 241 ± 10 nm | −36.2 ± 6.2 mV (pH 3.4) |

According to transmission electron micrograph (TEMs) analysis, the average size of the resulting capsaicin, nonivamide (pseudocapsaicin), arvanil, rinvanil, and resiniferatoxin nanoparticles after bath sonication synthesis in the absence of the calixarene-based compound template (4-tert-Butylcalix[4]arene) were 7±1 nm, 14±2 nm, 34±7 nm, 145±36 nm for nanorods and 28±4 nm for nanoparticles, and 17±3 nm, respectively.

Dynamic light scattering (DLS) and zeta potential of the drug nanoparticles was also assessed and the results are shown below in Table 1.

| Drug Nanoparticle | DLS (per intensity; 90° scattering) - without calixarene derivative | Zeta potential- without calixarene derivative |
|---|---|---|
| Capsaicin | 82 ± 10 nm and presence of larger size around 438 ± 45 nm | −17.0 ± 2.0 mV (pH: 7.2-7.7) |
| Nonivamide | 93 ± 1 nm and presence of larger size around 785 ± 83 nm | −20.3 ± 2.3 mV (pH: 7.5-7.6) |
| Arvanil | 328 ± 4 nm | −51.3 ± 1.5 mV (pH 7.2-7.6) |
| Rinvanil | 222 ± 20 nm | −39.8 ± 1.2 mV (pH 7.5-7.6) |
| Resiniferatoxin | 218 ± 13 nm | −35.8 ± 0.1 mV (pH 7.0) |

The data provided in this Example describes the generation of nanoscale average size for vanilloid compounds, after 24 hours of their synthesis using the bath sonication method and in presence and absence of the template: 4-tert-butylcalix[4]arene. The presence of the template delivered a better control over the morphology of the nanoparticles as shown by the TEM data. According to DLS, the template caused a decrease in size and improved the dispersity of the nanodrugs (especially for higher volume of the template (20 μL)). Zeta potential was improved especially for capsaicin and nonivamide (pseudocapsaicin). The zeta potential magnitude is expected to increase at higher pHs, which reflects better stability.

Example 2—In Vitro Cytotoxicity

About $1 \times 10^4$ TRPV1-overexpressed HEK293 (HEK293-TRPV1) cells/mL of medium were plated in four 96-well plates, and then incubated at 37° C. in a humidified, 5% $CO_2$ atmosphere. After 24 hours, a dilution plate of different concentrations of vanilloid nanoparticles were synthesized according to Example 1, as well as the negative control (without the drug, mostly water) was prepared. Each concentration of vanilloid nanoparticles was added into each well of the four well plates of cells that were prepared the previous day. After 0, 24, and 48 hours of incubation, an MTS reagent was added to each well plate, respectively, and followed by a 30 min to 1 hour incubation at 37° C. A Clariostar luminescent reader was used to measure the absorbance at 490 nm.

As shown in FIGS. 1A-1E, none of the vanilloid nanoparticles (capsaicin, nonivamide, arvanil, rinvanil, and RTX) repressed the proliferation of TRPV1-overexpressed HEK293 cells within 48 hours, confirming the absence of cytotoxicity of the nanoparticles. Further, the presence of calixarene derivative (4-tert-Butylcalix[4]arene) in the formulation of vanilloid nanoparticle did not cause any toxicity on the cells at the investigated concentrations. See FIGS. 1F-1K.

Conclusion: The present Example demonstrates that vanilloid nanoparticles (capsaicin, nonivamide, arvanil, rinvanil, and RTX) synthesized using bath sonication (with or without calixarene derivative template) as described in Example 1 (at a concentration range of 0 to 5 μM), did not repress the proliferation of TRPV1-overexpressed HEK293 cells within 48 hours, confirming the absence of cytotoxicity of the nanoparticles. Further, the presence of calixarene derivatives in the formulation of vanilloid nanoparticles did not cause any toxicity on the cells at the tested concentrations (0-5 μM).

Example 3—Calcium Influx Assay

TRPV1-overexpressed HEK293 cells (HEK293-TRPV1) were plated in a 96-well plate at a confluency of about $10^6$ cells/mL. A volume of 50 μL of cells was added to each well for 24 hours of incubation at 37° C. After 24 hours, the Fluo-4 reagent was added to each well (volume of 50 μL), followed by ~50 min incubation at 37° C. and a second ~15 min incubation at 25° C. A volume of either 10 μL of vanilloid nanoparticles (10 μM) or free vanilloid compounds as prepared according to Example 1 (i.e., vanilloid compounds not in nanoparticle form, also referred to as "bulk") was then injected into each well (final concentration equal to 0.1 μM). The fluorescence was measured and a time-response curve was generated in which the increase in fluorescence intensity was considered proportional to the efficiency of the agonist (rinvanil in this case). The efficacy of the nanoparticles was determined by comparing it to the effect observed with the bulk materials (the drug molecules were solubilized in a mixture of Ethanol/Water).

Figure 2:
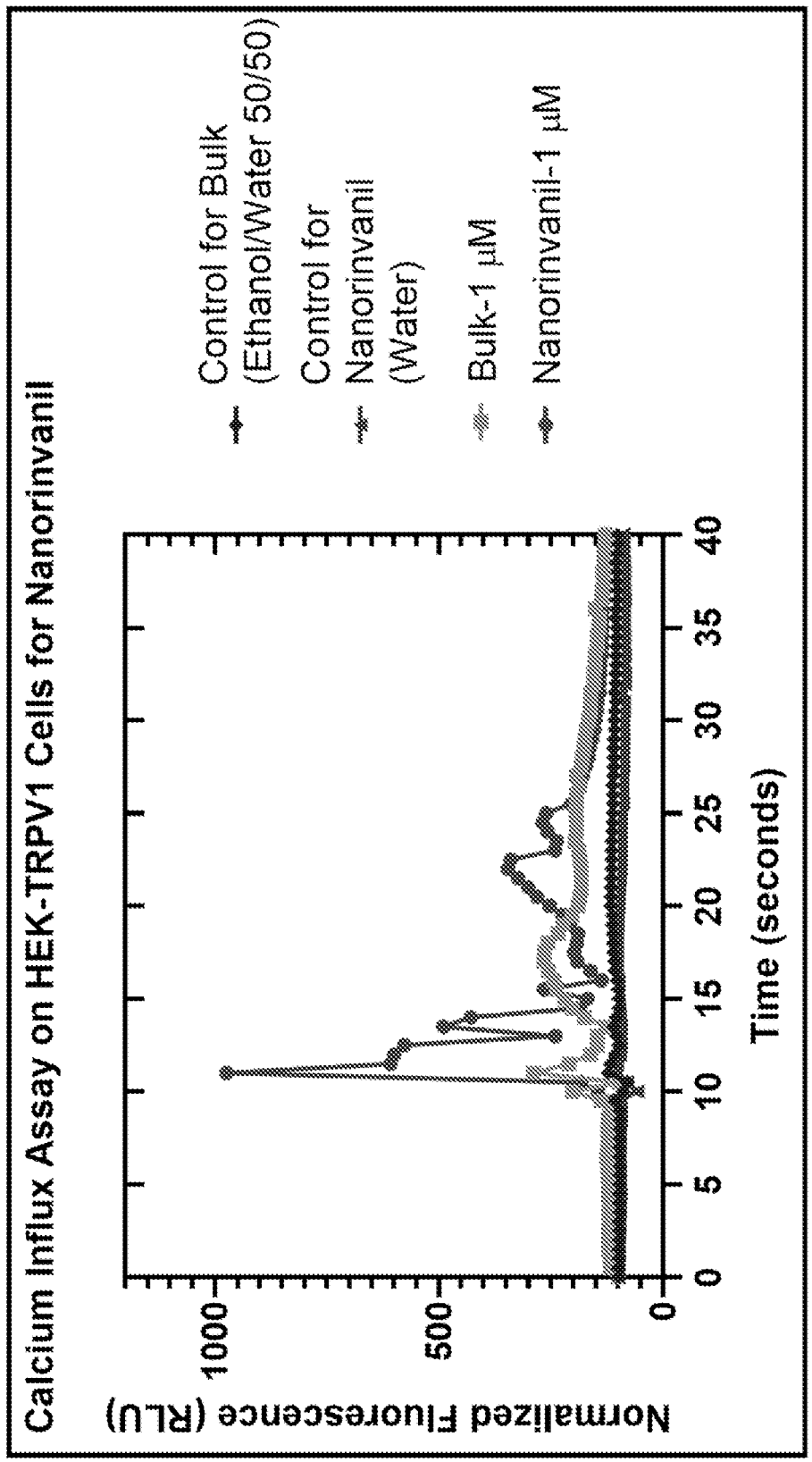
FIG. 2 is a graph showing the results of the experiment described in Example 3.

As shown in FIG. 2, the presence of rinvanil caused calcium influx upon activation of TRPV1 receptors, which was translated by an increase of fluorescence intensity in comparison to the control. The fluorescence intensity generated by the nanoparticles was 4 times higher (at 12.5 seconds) than the fluorescence caused by free (bulk) vanilloid molecules. The total surface area from 10 to 25 seconds corresponding to the vanilloid nanoparticles is twice higher than free (bulk) vanilloid molecules (i.e., vanilloid compounds not in nanoparticle form).

Conclusion: The interaction of rinvanil nanoparticles with the TRPV1 receptor was much more enhanced than the free molecules. Without wishing to be bound to any theory, it is contemplated that the enhanced interaction was due to the high loading capacity of the nanoparticle (assembly of several entities), causing subsequently an increase of activation efficiency.

Example 4—Stability Study

Rinvanil and resinferatoxin (RTX) nanoparticles were synthesized according to Example 1. The vials containing the nanoparticles were left on the bench for a week, without shaking. The vials were observed daily and photos were taken periodically (data not shown). There were no precipitates observed at the bottom of the vials after one week and also at twenty-five weeks at 25° C., showing that the nanoparticle formulation were shelf stable for at least that time period.

Example 5—In Vivo Studies

Synthesis of rinvanil nanoparticles: A volume of 5 µL of 20 mM ethanolic solution of rinvanil was added dropwise to 250 µL of distilled water in a vial under bath sonication. The sonication was for 5 minutes. A total of 4 suspensions were prepared to have several batches of rinvanil nanoparticles. The small vials were left covered with punctured parafilm for 24 hours. The vials were also jacketed by aluminum foil to avoid any possible photodegradation. After 24 hours, the suspensions were lyophilized (at least overnight). After the removal of water, the pellet was resuspended in 10.85 µL of water under sonication. The vials were left covered with aluminum foil until their application on animals. The final concentration in this case is 0.004 mg/µL of rinvanil nanoparticles (each vial).

Animal studies: The animals were initially anesthetized under the nose cone with 3.0% isoflurane and a mixture of 70/30 N20/oxygen. The tail artery was cannulated with PE-50 tubing to watch blood gases ($pO_2$ and $pCO_2$), blood pH, and glucose and mean arterial blood pressure (MABP). The animals were maintained with a mixture of 70% nitrous oxide, 30% oxygen and 0.5-2.0% isoflurane during the rest of the procedure. Physiological variables were adjusted in normal ranges 15 min prior the administration of the drug/control ($pO_2$ 105-140 mmHg, $pCO_2$ 35-45 mmHg, pH 7.35-7.45). The brain temperature (a probe inserted in the temporal muscle) and body temperature (rectal probe) were controlled at 37° C. with a feedback heat lamp system (the heat lamp was not used in initial experiments).

After 15 minutes of setting the physiological conditions, the nanoparticles and control (water) were administered in the nose. The heat lamp system was turned off to see how the temperature and the physiological variables changed over the course of two hours. Every 1 to 5 minutes, the temperature and blood pressure were recorded. The volume of nanoparticles suspension administered for animals depended on the final dosage needed and the weight of the animal. Usually the volume used was around 5 µL for a dosage of 0.05 mg/kg.

Figure 3A:
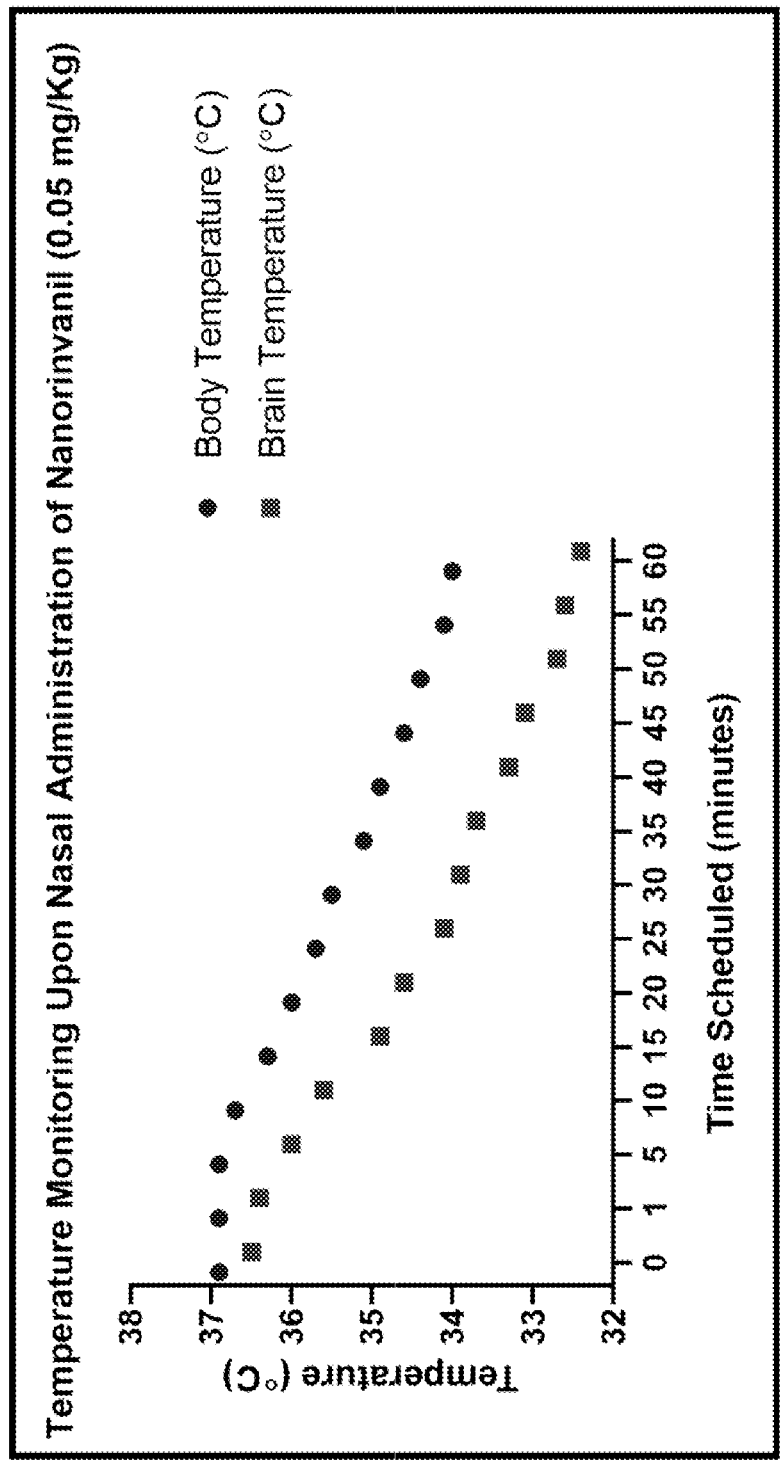
FIGS. 3A-3C provide the results of an in vivo study.

Acute reduction in brain and body temperature was observed following a single acute nasal administration of nanorinvanil (0.05 mg/kg). As shown in FIG. 3A, temperature is reduced by 3 degrees within 30 minutes of administration (N=1).

Figure 3B:
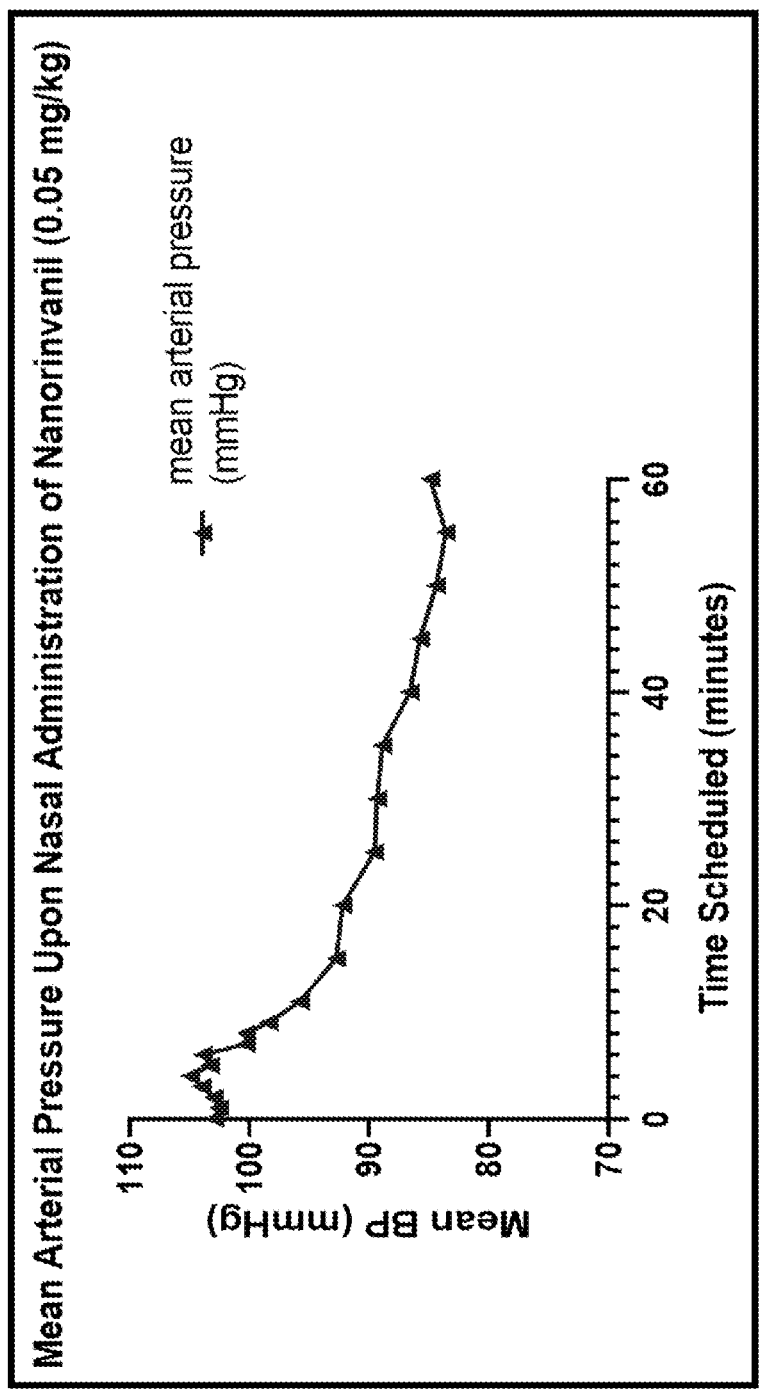
Figure 3C:
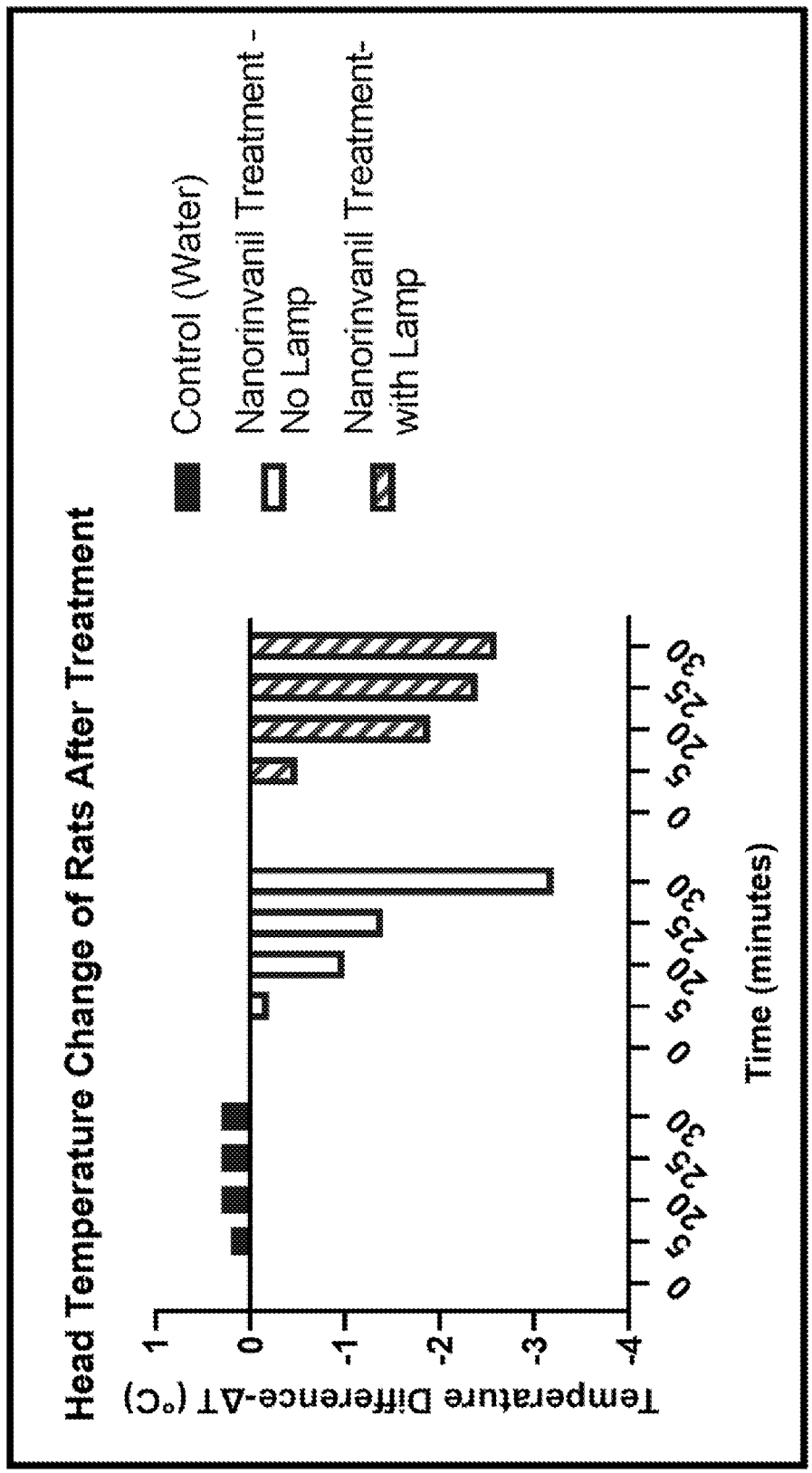

The head temperature drops after administration of nanorinvanil in comparison to the control (water). See FIG. 3C. The application of heat lamp during the experiments had a better control over the temperature drop (as shown by ΔT). The temperature decreased gradually when the heat lamp was applied. Mean arterial pressure decreased over time as well. See FIG. 3B.

All references and patent publications referenced herein are hereby incorporated by reference in their entireties.

REFERENCES CITED

1. Ahmed et al., *Neurosurg. Clin. N. Am.* 2016, 27, 489-497.
2. Dietrich et al., *Brain Res.* 2016, 1640, 94-103.
3. Marion et al., *J. Neurotrauma* 2009, 26, 455-467.
4. Dietrich et al., *Neurotherapeutics* 2011, 8, 229-239.
5. Wang et al., *Front. in Neuroscience* 2014, 8.
6. Lee et al., *J. Neurotrauma* 2014, 31, 1417-1430.
7. Gu et al., *Exp. Neurol.* 2015, 267, 135-142.
8. Liu et al., *Neurol. Res.* 2016, 38, 478-490.
9. Szolcsanyi, J. Effect of Capsaicin on Thermoregulation: an Update with New Aspects. *Temp. (Austin)* 2015, 2, 277-296.
10. Raisinghani et al., *The J. of Physiology* 2005, 567, 771-786.
11. Zhao et al., *J. Cell Physiol.* 2017, 232, 1957-1965.
12. Gavva et al., *J. Neurosci.* 2007, 27, 3366-3374.
13. Fosgerau et al., *BMC Card. Dis.* 2010, 10, 51.
14. Nakanishi, H.; Oikawa, H., Reprecipitation Method for Organic Nanocrystals. In *Single Organic Nanoparticles*, Masuhara, H.; Nakanishi, H.; Sasaki, K., Eds. Springer Berlin Heidelberg: Berlin, Heidelberg, 2003; pp 17-31.
15. Bharadwaj et al., *Sci. Rep.* 2016, 6, 29988.
16. Nakatsuji et al., *Angew Chem. Int. Ed. Engl.* 2015, 54, 11725-11729.
17. Truettner et al., *J. of Cerebral Blood Flow & Metabolism* 2016, 37, 2952-2962.
18. J. et al., Acta Neur. *Scandinavica* 2014, 129, 1-6.
19. Yokobori et al., *J. of Int. Care* 2016, 4, 28.
20. Zhu et al., *Spr. Plus* 2016, 5, 801.
21. Wang et al., *International journal of molecular sciences* 2015, 16, 16848-16879.
22. Sagalyn et al., *Crit. care med.* 2009, 37, S223-S226.
23. Latorre et al., *Curr. cardi. rep.* 2015, 17, 72.
24. Johansen et al., *Pathobiol.* 2014, 81, 42-52.
25. Diaz et al., *Anesthesia Prog.* 2010, 57, 25-33.
26. Romanovsky et al., *Pharmacol. Rev.* 2009, 61, 228-261.
27. Chen et al., *Adv. Mater.* 2015, 27, 903-910.
28. Hitoshi et al., *Angew. Chemie Int. Ed.* 2012, 51, 10315-10318.
29. Huang et al., *J. of the Am. Chem. Soc.* 2014, 136, 11748-11756.
30. Zhao et al., *ACS Appl. Mater. Interfaces* 2015, 7, 19295-19305.

31. Li et al., *Biomacromolecules* 2011, 12, 1724-1730.
32. You et al., *Oncotarget* 2017, 8, 29808-29822.
33. Chen et al., *ACS Nano* 2015, 9, 5223-5233.
34. Shen et al., *ACS Nano* 2016, 10, 5720-5729.
35. Sanna et al., *Int. J. of Nanomedicine* 2014, 9, 467-483.
36. Zhang et al., *Nano Lett.* 2015, 15, 313-318.
37. S, B., Nanoparticles Types, Classification, Characterization, Fabrication Methods and Drug Delivery Applications. In *Natural Polymer Drug Delivery Systems*, Springer, Cham: 2016.
38. Merisko-Liversidge et al., *Adv. Drug Deliv. Rev.* 2011, 63, 427-440.
39. Wu et al., *Adv. Drug Deliv. Rev.* 2011, 63, 456-469.
40. Kulkarni et al., *J. Drug Targ.* 2015, 23, 775-788.
41. Hanson et al., *BMC Neuroscience* 2008, 9, S5-S5.
42. Salatin et al., *Arch. Pharm. Res.* 2016, 39, 1181-1192.
43. Talegaonkar et al., *Indian J. of Pharm.* 2004, 36, 140-147.
44. Agrawal et al., *J. Control. Release* 2018, 281, 139-177.
45. Vercelli et al., *Recep. & Clini. Inv.* 2015, 2, 1-9.
46. Di Marzo et al., *J Pharmacol Exp Ther* 2002, 300, 984-991.
47. Chan et al., *Adv. Drug Deliv. Rev.* 2011, 63, 406-416.
48. Dieter et al., *Angew. Chem. Int. Ed.* 2001, 40, 4330-4361.
49. Wei et al., *Chem. Com. (Cambridge, England)* 2006, 1581-1591.
50. Chen et al., *Chem. of Mat.* 2014, 26, 941-950.
51. Yousaf et al., *Drug Des., Dev. and Ther.* 2015, 9, 2831-2838.
52. Iohara et al., *Mol. Pharm.* 2011, 8, 1276-1284.
53. Albanese et al., *Ann. Rev. of Biom. Eng.* 2012, 14, 1-16.
54. Sara et al., *Cell Biol. Int.* 2015, 39, 881-890.
55. Everett, D. H.; Everett, D., *Basic Principles of Colloid Science*. Royal Society of Chemistry London: 1988; Vol. 144.
56. Li et al., *Nature Nanot.* 2008, 3, 101-105.
57. Appendino et al., *J. of Pharm. and Exp. Therapeutics* 2005, 312, 561-570.
58. Grienberger et al., *Neuron* 2012, 73, 862-885.
59. Amidi et al., *J. of Controlled Release* 2006, 111, 107-116.
60. Davis et al., *Cl. Pharmacokinetics* 2003, 42, 1107-1128.
61. Guastella et al., *Psychoneuroendocrinology* 2013, 38, 612-625.
62. Kabadi et al., *Nature protocols* 2010, 5, 1552-1563.
63. Sakurai et al., *Journal of Neurotrauma* 2012, 29, 313-321.
64. Toth et al., *J Histochem Cytochem* 2014, 62, 129-144.
65. Vyklicky et al., *Physiol Res* 2008, 57 Suppl 3, S59-68.
66. Feketa et al., *Temp. (Austin)* 2015, 2, 244-257.

What is claimed is:

1. A method of inducing hypothermia in a subject in need thereof comprising administering to the subject a composition comprising a carrier-free nanoparticle comprising a vanilloid compound and an ion complexation agent, wherein said ion complexation agent is selected from the group consisting of calixarenes, crown ethers and calixcrowns, and wherein the nanoparticle has a particle size ranging from 4 nm to 100 nm in an amount effective to induce hypothermia in the subject.

2. The method of claim 1, wherein the vanilloid compound is capsaicin nonivamide, arvanil, rinvanil or resiniferatoxin.

3. The method of claim 1, wherein the ion complexation agent is 4-tert-butylcalix[4]arene.

4. The method of claim 1, wherein the composition is administered intranasally.

5. The method of claim 1, wherein the composition is administered as a nasal spray.

6. The method of claim 1, wherein the subject has suffered brain trauma, cardiac arrest, spinal cord injury, epilepsy or a stroke.

* * * * *